United States Patent
Shimokawa et al.

(10) Patent No.: US 10,935,563 B2
(45) Date of Patent: Mar. 2, 2021

(54) VASCULAR SAP FLOW SPEED SENSOR AND METHOD OF MANUFACTURING VASCULAR SAP FLOW SPEED SENSOR

(71) Applicant: NATIONAL UNIVERSITY CORPORATION KAGAWA UNIVERSITY, Kagawa (JP)

(72) Inventors: Fusao Shimokawa, Kagawa (JP); Kyosuke Nakada, Kagawa (JP); Hidekuni Takao, Kagawa (JP); Kyohei Terao, Kagawa (JP); Hidenori Yoshimura, Kagawa (JP); Hiroki Ishizuka, Kagawa (JP); Tsuyoshi Kobayashi, Kagawa (JP); Ikuo Kataoka, Kagawa (JP)

(73) Assignee: NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 0 days.

(21) Appl. No.: 16/493,178

(22) PCT Filed: Mar. 1, 2018

(86) PCT No.: PCT/JP2018/007693
§ 371 (c)(1),
(2) Date: Sep. 11, 2019

(87) PCT Pub. No.: WO2018/168483
PCT Pub. Date: Sep. 20, 2018

(65) Prior Publication Data
US 2020/0081026 A1 Mar. 12, 2020

(30) Foreign Application Priority Data
Mar. 13, 2017 (JP) .............................. JP2017-046926

(51) Int. Cl.
*G01P 5/12* (2006.01)
*G01K 13/02* (2006.01)
(Continued)

(52) U.S. Cl.
CPC .................. *G01P 5/12* (2013.01); *A01G 7/00* (2013.01); *G01F 1/684* (2013.01); *G01K 13/02* (2013.01);
(Continued)

(58) Field of Classification Search
CPC ...... G01R 3/00; G01R 1/067; G01R 1/07307; G01R 1/0675; G01R 1/06738; G01R 31/2874; G01R 1/07314; G01R 1/0735
See application file for complete search history.

(56) References Cited

U.S. PATENT DOCUMENTS 2,777,325 A * 1/1957 Bockmeulen ........... G01F 1/684
73/204.15
4,135,396 A * 1/1979 Stanke .................... G01F 1/696
73/204.19
(Continued)

FOREIGN PATENT DOCUMENTS

CN 201225998 Y * 4/2009
FR 2582811 A1 * 12/1986 ......... G01N 33/0098
(Continued)

OTHER PUBLICATIONS

WIPO, International Search Report for PCT Application No. PCT/JP2018/007693, dated May 29, 2018.

*Primary Examiner* — Ryan D Walsh

(57) ABSTRACT

To provide a vascular sap flow speed sensor having a size allowing measurement of the flow speed of vascular sap in a part of a plant such as a stem and capable of being manufactured at low cost. A vascular sap flow speed sensor 1 includes a heater sensor HS and a reference sensor RS. The
(Continued)

heater sensor HS includes: a first probe unit 10*a* including a heat transfer plate 11 and a probe 12; a heater 20; a first temperature sensor 30*a*; and a first housing 40*a* in which the heat transfer plate 11, the heater 20, and the first temperature sensor 30*a* are housed. The reference sensor RS includes: a second probe unit 10*b* including a heat transfer plate 11 and a probe 12; a second temperature sensor 30*b*; and a second housing 40*b* in which the heat transfer plate 11 and the second temperature sensor 30*b* are housed. Each of the first probe unit 10*a* and the second probe unit 10*b* is made of a metallic material.

18 Claims, 15 Drawing Sheets

(51) Int. Cl.
*A01G 7/00* (2006.01)
*G01F 1/684* (2006.01)
*G01N 33/00* (2006.01)

(52) U.S. Cl.
CPC ... *G01N 33/0098* (2013.01); *G01K 2013/026* (2013.01)

(56) References Cited

U.S. PATENT DOCUMENTS

| | | | |
|---|---|---|---|
| 4,480,467 A * | 11/1984 | Harter | G01F 1/684 340/606 |
| 5,269,183 A | 12/1993 | Van Bavel | |
| 6,588,268 B1 | 7/2003 | Yamagishi et al. | |
| 2017/0001029 A1 | 1/2017 | Pribula et al. | |
| 2019/0257681 A1* | 8/2019 | Lee | G01N 33/0098 |

FOREIGN PATENT DOCUMENTS

| | | | | |
|---|---|---|---|---|
| JP | H05-188070 A | | 7/1993 | |
| JP | H06-273434 A | | 9/1994 | |
| JP | 2000-146653 A | | 5/2000 | |
| JP | 2014-211407 A | | 11/2014 | |
| JP | 2015-145810 A | | 8/2015 | |
| JP | 2017074023 A | * | 4/2017 | |
| WO | WO-0239071 A1 | * | 5/2002 | G01F 1/684 |

* cited by examiner

F I G. 1
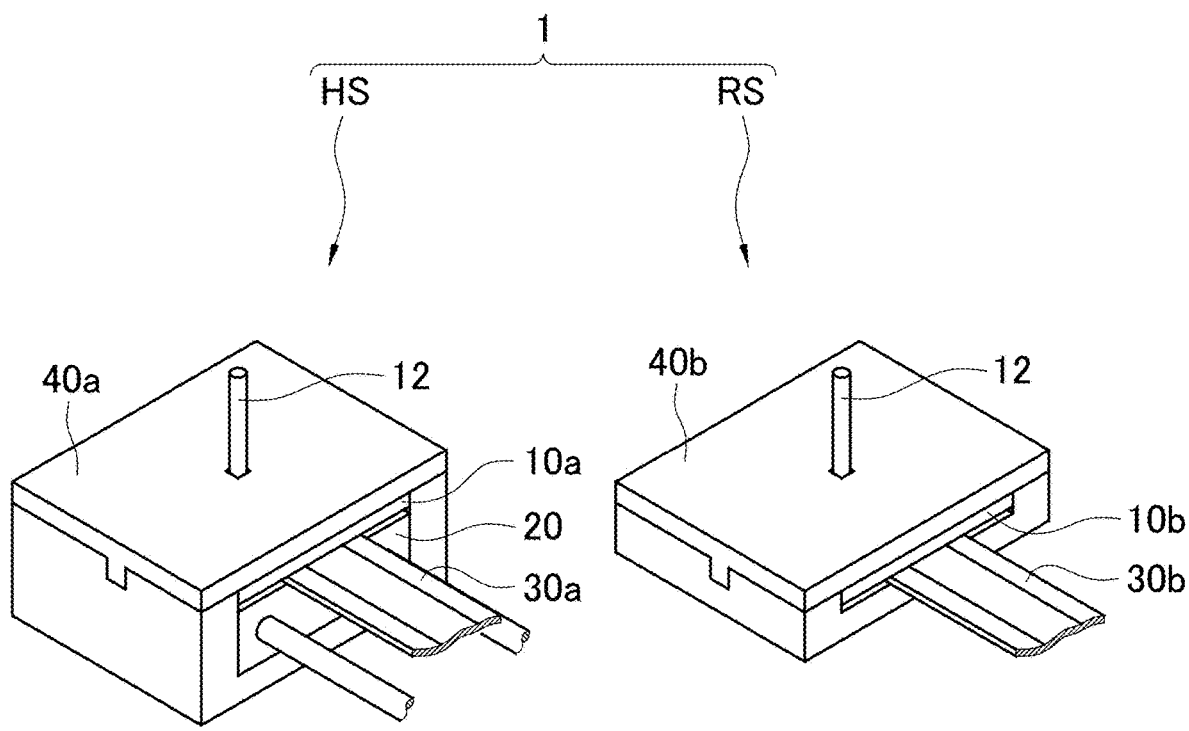

F I G. 3 A
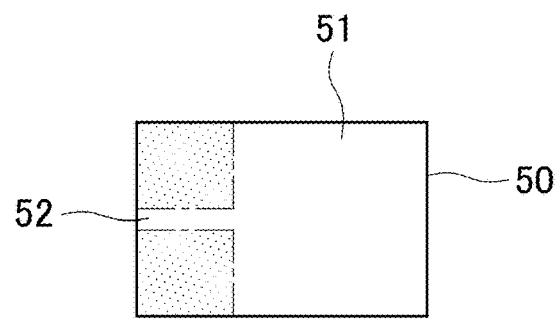
F I G. 3 B
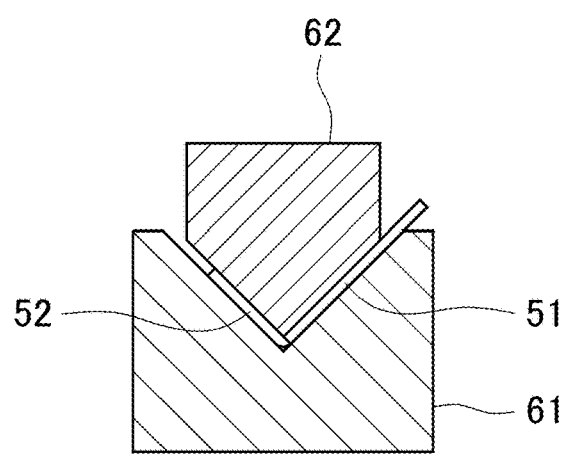
F I G. 3 C
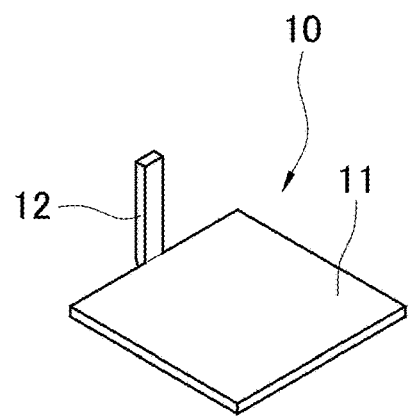

F I G. 4 A
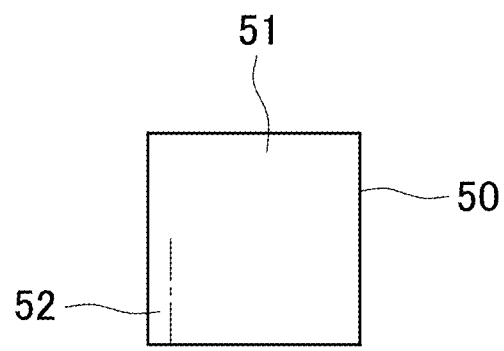
F I G. 4 B
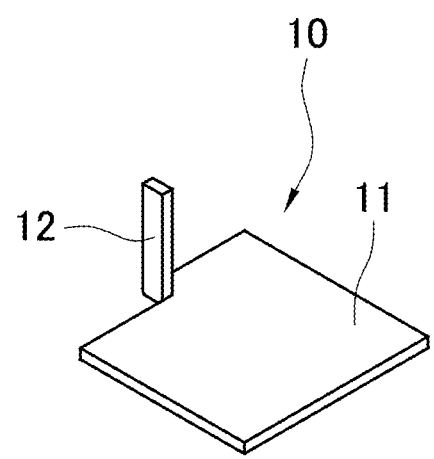

F I G. 6 A
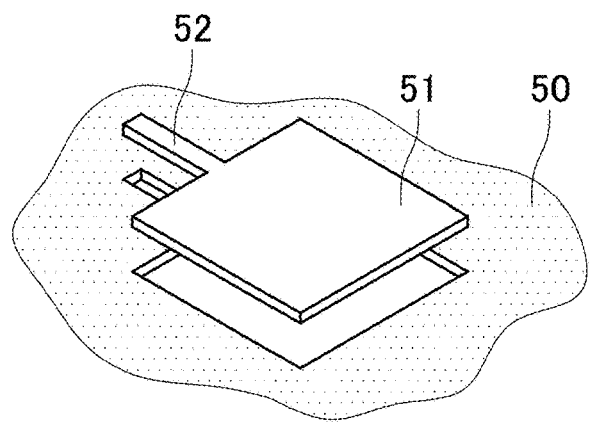
F I G. 6 B
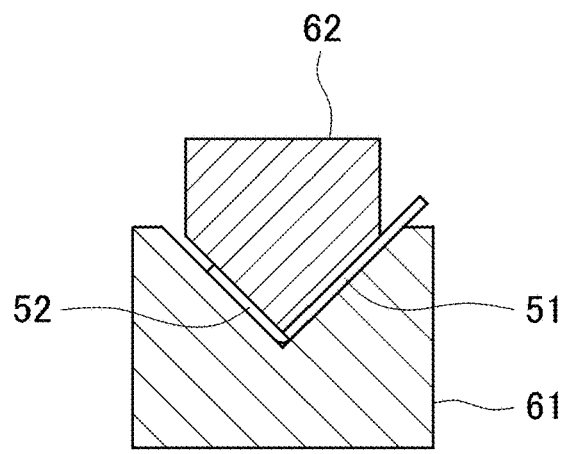
F I G. 6 C
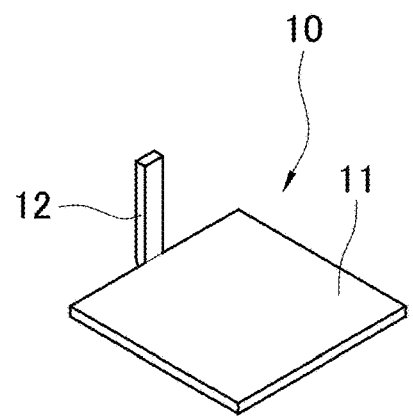

F I G. 8 A
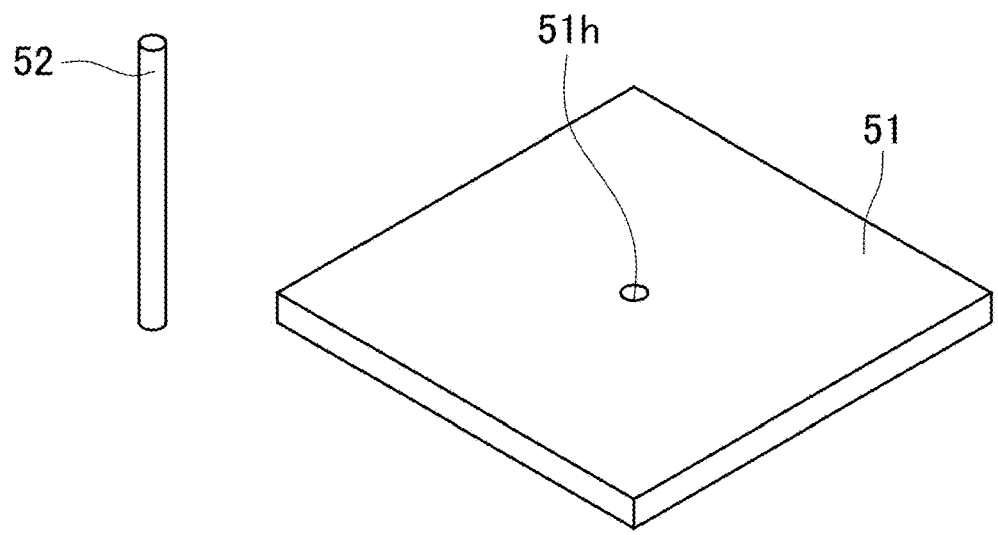
F I G. 8 B
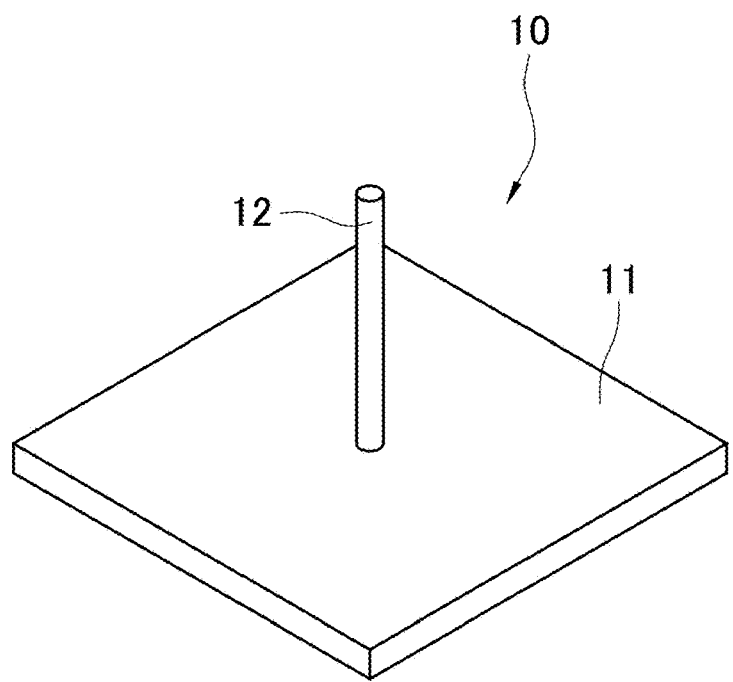

VASCULAR SAP FLOW SPEED SENSOR AND METHOD OF MANUFACTURING VASCULAR SAP FLOW SPEED SENSOR

TECHNICAL FIELD

This invention relates to a vascular sap flow speed sensor and a method of manufacturing the vascular sap flow speed sensor. More specifically, this invention relates to a vascular sap flow speed sensor for measurement of the flow speed of vascular sap in a new branch or a stem leading to the new branch of a plant, for example, and a method of manufacturing the vascular sap flow speed sensor.

BACKGROUND ART

In production of crops, fruit, and the like, a plant needs to be supplied with water or replenished with nutrients at appropriate times that depend on the growing condition of the plant, from the viewpoint of enhancing productivity. Thus, grasping the growing condition of the plant properly without inhibiting the growing of the plant is considerably important.

An actual situation in many agricultural sites is that the growing condition of a plant is generally grasped according to experience or by intuition based on the number of days without rain or change in climate or temperature, for example. However, managing the growing condition of a plant by a method based on experience, and the like is skillful work that involves much expense in time and effort. Additionally, such management uses indexes as a reference that are determined based on personal experience, for example. Hence, not everyone finds it easy to implement such a method of grasping the growing condition of a plant based on experience, etc.

On the other hand, various techniques have been developed in recent years intended to execute water control or fertilization management of crops or fruit based on biological information about a plant. Among these techniques, there is a notable measuring method using the Granier method. There is also a known method of measuring the flow speed of sap using the heat pulse method (see patent literature 1, for example).

Patent literature 1 discloses a device with three rod-shaped temperature sensors and one rod-shaped heater that can be located in holes formed in a trunk of a tree with a drill, for example. According to a technique disclosed in patent literature 1, the temperature sensors and the rod-shaped heater of the device are located in holes formed in a sapwood part of the tree. After passage of a predetermined time, the flow speed of sap flowing in the tree is measured based on a temperature difference between these sensors.

The device of patent literature 1 has originally been developed for measurement of the flow speed of sap flowing in a tree having a relatively large stem diameter, and the rod-shaped sensors used in this device have certain degrees of size. Hence, the device of patent literature 1 is not easily applicable to a new branch or a stem leading to the new branch, for example, with a stem diameter of about several millimeters.

Measuring the flow rate of vascular sap in a plant is important for grasping the growing condition of the plant. In particular, grasping the flow rate of vascular sap in a part having a diameter of about several millimeters such as a distal end of a new branch, a pedicel, a stem leading to the new branch or pedicel is considerably important for enhancing the productivity and the quality of crops, fruit, and the like.

The present inventors have devised a plant water dynamics sensor usable for measuring the dynamics of vascular sap (dynamics of water or nutrient solution) flowing in a fine point of a plant such as a distal end of a new branch or a pedicel (patent literature 2). Patent literature 2 discloses a plant water dynamics sensor with a probe formed into a size allowing the probe to be stuck into a distal end of a new branch, a pedicel, etc. The water dynamics (the flow rate and the direction of vascular sap) can be measured using the Granier method by sticking and locating the probe in a stem of a plant, for example.

CITATION LIST

Patent Literatures

Patent Literature 1: Japanese Patent Application Publication No. Hei 6-273434
Patent Literature 2: Japanese Patent Application Publication No. 2014-211407

SUMMARY OF INVENTION

Technical Problem

The plant water dynamics sensor of patent literature 2 is formed by processing a semiconductor substrate by the MEMS technology. This causes increase in manufacturing cost in the case of low-volume production.

If a probe is formed by processing a semiconductor substrate by the MEMS technology, the length of the resultant probe is generally about several hundreds of micrometers. In many existing plants, however, a distance from the cortex of a stem to a vascular bundle in the stem exceeds 1 mm. In such plants, using the conventional plant water dynamics sensor is not usable for measuring the dynamics of vascular sap.

In view of the foregoing circumstances, this invention is intended to provide a vascular sap flow speed sensor having a size allowing measurement of the flow speed of vascular sap in a part of a plant such as a stem and capable of being manufactured at low cost, and a method of manufacturing the vascular sap flow speed sensor.

This invention is also intended to provide a vascular sap flow speed sensor usable for measuring the flow speed of vascular sap even in a plant in which a cortex is at a long distance from a vascular bundle, and a method of manufacturing the vascular sap flow speed sensor.

Solution to Problem

A vascular sap flow speed sensor according to a first invention includes a heater sensor and two reference sensors. The heater sensor includes: a first probe unit including a heat transfer plate and a probe provided in an upright posture at the heat transfer plate; a heater that supplies heat to the heat transfer plate of the first probe unit; a first temperature sensor that measures a temperature at the heat transfer plate of the first probe unit; and a first housing in which the heat transfer plate of the first probe unit, the heater, and the first temperature sensor are housed and from which the probe of the first probe unit is exposed to the outside. Each of the two reference sensors includes: a second probe unit including a heat transfer plate and a probe provided in an upright posture at the heat transfer plate; a second temperature sensor that measures a temperature at the heat transfer plate of the second probe unit; and a second housing in which the heat transfer plate of the second probe unit and the second temperature sensor are housed and from which the probe of the second probe unit is exposed to the outside. The probe of the first probe unit and the probe of the second probe unit have the same length. Each of the first probe unit and the second probe unit is made of a metallic material. The two reference sensors are arranged at positions between which the heater sensor is located during attachment to a plant.

The vascular sap flow speed sensor according to a second invention is characterized in that, in the first invention, the length of each of the probe of the first probe unit and the probe of the second probe unit is from 1 to 5 mm.

The vascular sap flow speed sensor according to a third invention is characterized in that, in the first or second invention, the vascular sap flow speed sensor includes a housing with the first housing and the two second housings integrated with each other. The probe of the first probe unit and the probes of the two second probe units are aligned along one surface of the housing. The probes of the two second probe units are arranged at positions between which the probe of the first probe unit is located.

The vascular sap flow speed sensor according to a fourth invention is characterized in that, in any of the first to third inventions, each of the first probe unit and the second probe unit is formed by machining a single metallic plate into the heat transfer plate and the probe.

The vascular sap flow speed sensor according to a fifth invention is characterized in that, in the fourth invention, each of the first probe unit and the second probe unit is made of the single metallic plate with a heat transfer plate corresponding part and a probe corresponding part, and a connection between the heat transfer plate corresponding part and the probe corresponding part is bent.

A vascular sap flow speed sensor according to a sixth invention includes a heater sensor and a reference sensor. The heater sensor includes: a first probe unit including a heat transfer plate and a probe provided in an upright posture at the heat transfer plate; a heater that supplies heat to the heat transfer plate of the first probe unit; a first temperature sensor that measures a temperature at the heat transfer plate of the first probe unit; and a first housing in which the heat transfer plate of the first probe unit, the heater, and the first temperature sensor are housed and from which the probe of the first probe unit is exposed to the outside. The reference sensor includes: a second probe unit including a heat transfer plate and a probe provided in an upright posture at the heat transfer plate; a second temperature sensor that measures a temperature at the heat transfer plate of the second probe unit; and a second housing in which the heat transfer plate of the second probe unit and the second temperature sensor are housed and from which the probe of the second probe unit is exposed to the outside. The probe of the first probe unit and the probe of the second probe unit have the same length. Each of the first probe unit and the second probe unit includes the heat transfer plate and the probe formed by providing a projection at a part of the single metallic plate by deep drawing.

A vascular sap flow speed sensor according to a seventh invention includes a heater sensor and a reference sensor. The heater sensor includes: a first probe unit including a heat transfer plate and a probe provided in an upright posture at the heat transfer plate; a heater that supplies heat to the heat transfer plate of the first probe unit; a first temperature sensor that measures a temperature at the heat transfer plate of the first probe unit; and a first housing in which the heat transfer plate of the first probe unit, the heater, and the first temperature sensor are housed and from which the probe of the first probe unit is exposed to the outside. The reference sensor includes: a second probe unit including a heat transfer plate and a probe provided in an upright posture at the heat transfer plate; a second temperature sensor that measures a temperature at the heat transfer plate of the second probe unit; and a second housing in which the heat transfer plate of the second probe unit and the second temperature sensor are housed and from which the probe of the second probe unit is exposed to the outside. The probe of the first probe unit and the probe of the second probe unit have the same length. Each of the first probe unit and the second probe unit is formed by joining a probe corresponding part made of a metallic wire rod to a heat transfer plate corresponding part made of a metallic plate.

The vascular sap flow speed sensor according to an eighth invention is characterized in that, in any of the first to seventh inventions, the heater has an area same as or larger than that of the heat transfer plate of the first probe unit.

The vascular sap flow speed sensor according to a ninth invention is characterized in that, in any of the first to eighth inventions, each of the first temperature sensor and the second temperature sensor is a sheet-like material provided with a temperature detection element.

The vascular sap flow speed sensor according to a tenth invention is characterized in that, in any of the first to seventh inventions, the heater and the first temperature sensor are formed on a semiconductor substrate having an area same as or larger than that of the heat transfer plate of the first probe unit.

The vascular sap flow speed sensor according to an eleventh invention is characterized in that, in any of the first to seventh inventions, the second temperature sensor is formed on a semiconductor substrate having an area same as or larger than that of the heat transfer plate of the second probe unit.

The vascular sap flow speed sensor according to a twelfth invention is characterized in that, in any of the first to eleventh inventions, each of the first housing and the second housing is made of a material having lower heat conductivity than a material forming each of the first probe unit and the second probe unit.

A method of manufacturing a vascular sap flow speed sensor according to a thirteenth invention includes: a probe unit forming step of obtaining a first probe unit and a second probe unit by forming a plurality of probe units each including a heat transfer plate and a probe provided in an upright posture at the heat transfer plate using a metallic material; a heater sensor assembling step of assembling a heater sensor by providing a heater and a first temperature sensor at the heat transfer plate of the first probe unit, and housing the heat transfer plate of the first probe unit, the heater, and the first temperature sensor into a first housing in such a manner as to expose the probe of the first probe unit to the outside from the first housing; a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing; and configuring the vascular sap flow speed sensor using the heater sensor, and the two reference sensors arranged at positions between which the heater sensor is located during attachment to a plant.

The method of manufacturing the vascular sap flow speed sensor according to a fourteenth invention is characterized in that, in the thirteenth invention, the probe unit forming step includes: a plate processing step of processing a metallic plate to form a heat transfer plate corresponding part and a probe corresponding part; and a bending step of bending a connection between the heat transfer plate corresponding part and the probe corresponding part.

The method of manufacturing the vascular sap flow speed sensor according to a fifteenth invention is characterized in that, in the fourteenth invention, in the plate processing step, the metallic plate is cut by laser machining to form the heat transfer plate corresponding part and the probe corresponding part.

The method of manufacturing the vascular sap flow speed sensor according to a sixteenth invention is characterized in that, in the fourteenth invention, in the plate processing step, the metallic plate is stamped by pressing to form the heat transfer plate corresponding part and the probe corresponding part.

A method of manufacturing a vascular sap flow speed sensor according to a seventeenth invention includes: a probe unit forming step of obtaining a first probe unit and a second probe unit by forming a plurality of probe units each including a heat transfer plate and a probe provided in an upright posture at the heat transfer plate using a metallic material; a heater sensor assembling step of assembling a heater sensor by providing a heater and a first temperature sensor at the heat transfer plate of the first probe unit, and housing the heat transfer plate of the first probe unit, the heater, and the first temperature sensor into a first housing in such a manner as to expose the probe of the first probe unit to the outside from the first housing; and a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing. The probe unit forming step includes a step of providing a projection as the probe by performing deep drawing on a metallic plate.

A method of manufacturing a vascular sap flow speed sensor according to an eighteenth invention includes: a probe unit forming step of obtaining a first probe unit and a second probe unit by forming a plurality of probe units each including a heat transfer plate and a probe provided in an upright posture at the heat transfer plate using a metallic material; a heater sensor assembling step of assembling a heater sensor by providing a heater and a first temperature sensor at the heat transfer plate of the first probe unit, and housing the heat transfer plate of the first probe unit, the heater, and the first temperature sensor into a first housing in such a manner as to expose the probe of the first probe unit to the outside from the first housing; and a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing. The probe unit forming step includes: a step of cutting a metallic plate to form a heat transfer plate corresponding part; a step of cutting a metallic wire rod to form a probe corresponding part; and a step of joining the probe corresponding part to the heat transfer plate corresponding part.

Advantageous Effects of Invention

According to the first invention, the heater and the temperature sensor are provided at the heat transfer plate where the probe is provided in an upright posture. This configuration facilitates transfer of heat between the probe and the heater and between the probe and the temperature sensor and can achieve size reduction of the probe, compared to a conventional configuration in which a heater and a temperature sensor are directly provided at a probe. Thus, it becomes possible to measure the flow speed of vascular sap in a fine point of a plant. Further, the simple configuration of the vascular sap flow speed sensor allows manufacture at low cost. Still further, the presence of the two reference sensors allows measurement of a direction in which vascular sap flows.

According to the second invention, the length of the probe is from 1 to 5 mm. Thus, even in a plant in which a cortex is at a long distance from a vascular bundle, the flow speed of vascular sap can still be measured.

According to the third invention, as the heater sensor and the reference sensor are formed integrally, attachment of the vascular sap flow speed sensor to a plant is facilitated.

According to the fourth invention, as the probe unit is made of a single metallic plate, the probe unit can be manufactured at low cost.

According to the fifth invention, as the probe unit is formed by bending the metallic plate, the probe unit can be manufactured at low cost.

According to the sixth invention, as the probe is formed by providing a projection at a part of the metallic plate, the probe unit can be manufactured at low cost.

According to the seventh invention, as the probe unit is formed using the metallic plate and the metallic wire rod, the probe unit can be manufactured at low cost.

According to the eighth invention, an area of contact between the heater and the heat transfer plate is increased to allow supply of heat of the heater efficiently to the probe unit.

According to the ninth invention, as a commercially-available film temperature sensor is used, the vascular sap flow speed sensor can be manufactured at low cost.

According to the tenth invention, forming the heater and the first temperature sensor on the semiconductor substrate allows size reduction. Further, manufacturing cost can be reduced.

According to the eleventh invention, forming the second temperature sensor on the semiconductor substrate allows size reduction. Further, manufacturing cost can be reduced.

According to the twelfth invention, as the housing is made of the material having low heat conductivity, high heat insulating properties are provided.

According to the thirteenth invention, as the simple constituting members are used and the simple manufacturing steps are employed, the vascular sap flow speed sensor can be manufactured at low cost.

According to the fourteenth invention, as the probe unit is formed by bending on the metallic plate, the probe unit can be manufactured at low cost.

According to the fifteenth invention, as the probe unit is formed by laser machining on the metallic plate, the probe unit can be manufactured at low cost.

According to the sixteenth invention, as the probe unit is formed by stamping the metallic plate, the probe unit can be manufactured at low cost.

According to the seventeenth invention, as the probe unit is formed by deep drawing on the metallic plate, the probe unit can be manufactured at low cost.

According to the eighteenth invention, as the probe unit is formed using the metallic plate and the metallic wire rod, the probe unit can be manufactured at low cost.

BRIEF DESCRIPTION OF DRAWINGS

FIG. 1 is a perspective view of a vascular sap flow speed sensor according to a first embodiment of this invention.

FIG. 3A is an explanatory view of laser machining.
FIG. 3B is an explanatory view of bending.
FIG. 3C is a perspective view of a probe unit.
FIG. 4A is an explanatory view of laser machining.
FIG. 4B is a perspective view of the probe unit.
FIG. 6A is an explanatory view of stamping.
FIG. 6B is an explanatory view of bending.
FIG. 6C is a perspective view of the probe unit.
FIG. 8A is an explanatory view of processing on a metallic plate and a metallic wire rod.
FIG. 8B is a perspective view of the probe unit.

DESCRIPTION OF EMBODIMENTS

Figure 2:
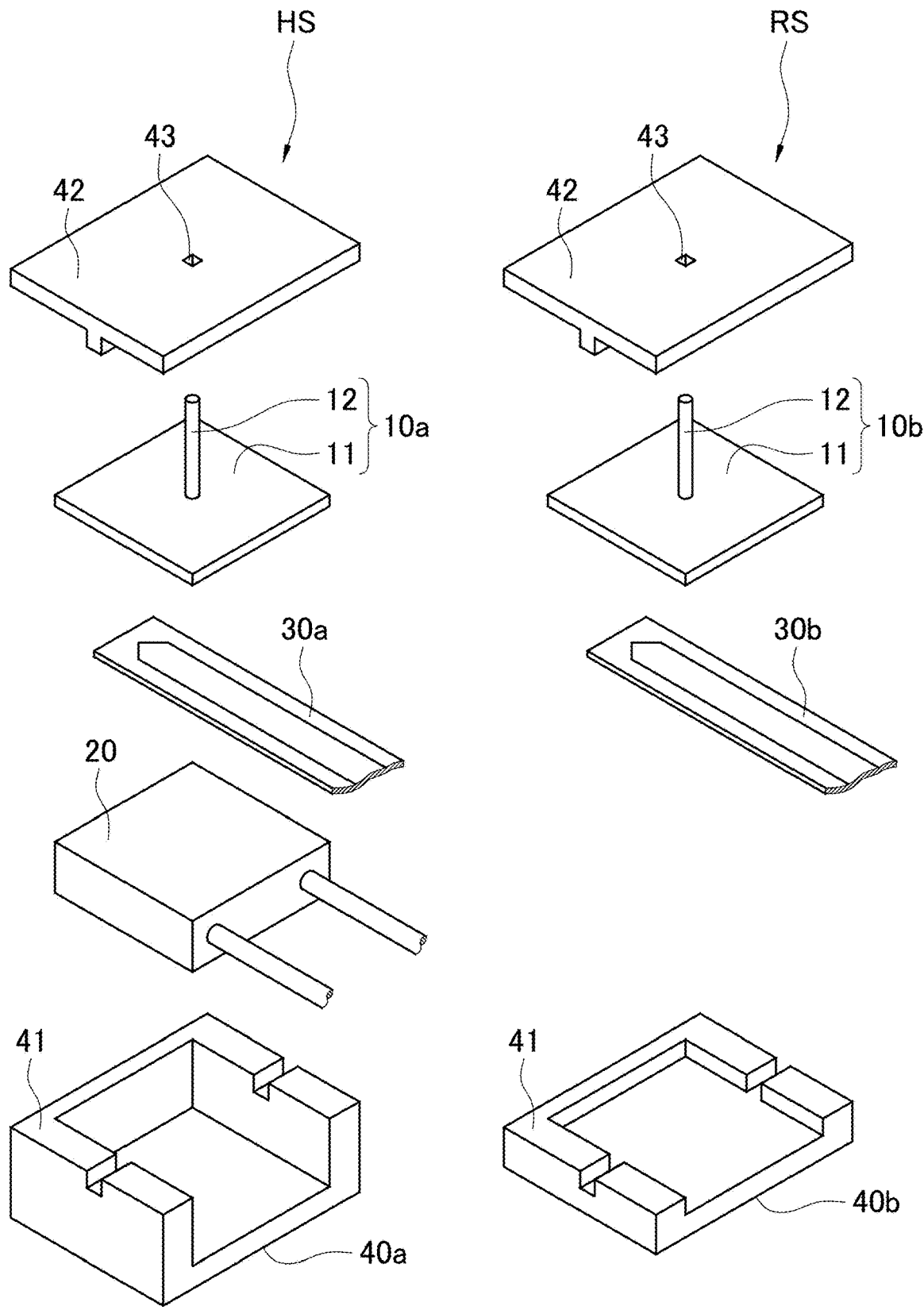
FIG. 2 is an exploded perspective view of the vascular sap flow speed sensor.

Embodiments of this invention are described next based on the drawings.

First Embodiment

A vascular sap flow speed sensor 1 according to a first embodiment of this invention can be attached easily to a fine point of a plant such as a distal end of a new branch (hereinafter simply called a new branch distal end) or a pedicel of the plant. The vascular sap flow speed sensor 1 has a function of measuring the flow speed of vascular sap in the fine point of the plant.

(Granier Method)

The vascular sap flow speed sensor 1 is used for measuring the flow speed of vascular sap in a plant using the Granier method. Principles of determining the flow speed of sap flowing in a tree and determining a flow rate from the flow speed using the Granier method will be described briefly.

The Granier method is to calculate a sap flow rate F using a Granier sensor. The Granier sensor includes rod-shaped probes in a pair. These probes in a pair each include a temperature sensor. One of the probes in a pair includes a heater. The probe with the temperature sensor and the heater will be called a heater probe HP. The other probe is a probe used for reference. The probe only including the temperature sensor will be called a reference probe RP.

A method of installing the Granier sensor on a tree and measuring the sap flow rate F in the tree will be described below.

First, holes are formed in two places of the trunk of the tree with a drill, for example. The heater probe HP and the reference probe RP of the Granier sensor are inserted in the corresponding holes to be installed on the tree and left at rest for one day or more. The reference probe RP and the heater probe HP of the Granier sensor are aligned in this order along a sap flow in a direction from an upstream side toward a downstream side. More specifically, if sap flows in a direction from a root toward a distal end, the reference probe RP is inserted in a hole closer to the root and the heater probe HP is inserted in a hole closer to the distal end.

Next, the heater of the heater probe HP of the Granier sensor is actuated. This generates temperature difference ΔT between the respective temperature sensors of the probes HP and RP in a pair. As shown by the following formula 1, the temperature difference ΔT is used as a function of a sap flow speed u. By using this function as a basis, the sap flow speed u can be calculated from the temperature difference ΔT.

[Formula 1]

$$u = \frac{1}{\alpha}\left\{\frac{\Delta T(0) - \Delta T(u)}{\Delta T(u)}\right\}^{\frac{1}{\beta}} = \frac{1}{\alpha}K^{\frac{1}{\beta}} \qquad (1)$$

In this formula, u is an average sap flow speed [m/s], ΔT(u) is temperature difference [° C.] between the heater probe HP and the reference probe RP determined if an average sap flow speed is u, ΔT(0) is a maximum temperature [° C.] of ΔT, and α and β are coefficients obtained from observed data.

On the basis of the following formula 2, the sap flow rate F can be calculated using the sap flow speed u.

[Formula 2]

$$F = u \times S \qquad (2)$$

In this formula, F is a sap flow rate [m³/s], and S is a cross-sectional area [m²] formed by the probes HP and RP in a peripheral direction of a trunk.

If the flow rate F of sap flowing in a tree is high (if the sap flow speed u is high), for example, the temperature difference ΔT between the respective temperature sensors of the probes HP and RP in a pair of the Granier sensor is small. This is because, while the heater applies constant heat to the heater probe HP, this heat is carried away by a large quantity of sap flowing in the vicinity of the heater probe HP. Meanwhile, if the sap flow rate F is low (if the sap flow speed u is low), the temperature difference ΔT between the respective temperature sensors of the probes HP and RP in a pair of the Granier sensor is large. This is because, while the heater applies constant heat to the heater probe HP, this heat supplied to the heater probe HP stays without being carried away by sap as the sap flows in small quantity in the vicinity of the heater probe HP.

(Vascular Sap Flow Speed Sensor)

The vascular sap flow speed sensor 1 of the first embodiment will be described next.

As shown in FIGS. 1 and 2, the vascular sap flow speed sensor 1 includes a heater sensor HS and a reference sensor RS.

The heater sensor HS includes a first probe unit 10a, a heater 20, a first temperature sensor 30a, and a first housing 40a. The first probe unit 10a includes a heat transfer plate 11 and a probe 12 provided in an upright posture at the heat transfer plate 11. The shape of the heat transfer plate 11 is not particularly limited but it may be a rectangle, for example. Regarding the size of the heat transfer plate 11, the heat transfer plate 11 is from 2 to 100 mm in length and width, for example.

The probe 12 is a rod-like member. The probe 12 may be a circular column or a prism. The probe 12 is formed into a size that allows the probe 12 to be stuck into and installed on a stem of a plant such as a new branch distal end or a pedicel. The vascular sap flow speed sensor 1 of the first embodiment is intended for measurement of a plant having a stem diameter or an axis diameter from about 1 to about 10 mm, for example. The probe 12 is formed into a length that allows a tip portion of the probe 12 to be located in a xylem or a phloem in the stem, etc. of the plant while the probe 12 is stuck into and installed on this stem of the plant. Thus, the length of the probe 12 is preferably from 0.5 to 5 mm, for example.

Damage (injury) to a plant can be alleviated further by making the probe 12 thinner. If the probe 12 has a circular columnar shape, the diameter of the probe 12 is preferably from 100 to 1,000 µm, for example. However, the diameter of the probe 12 is not necessarily limited to this size. The diameter of the probe 12 may be more than 1,000 µm or less than 100 µm in response to a stem diameter of a plant to be measured. If the probe 12 has a quadrangular columnar shape, a length-to-width ratio of its cross section is preferably from 1:1 to 1.3.

The first probe unit 10a is made of a metallic material having high heat conductivity. More specifically, the heat transfer plate 11 is made of a metallic plate, and the probe 12 is made of a metallic probe. Metal forming the first probe unit 10a is not particularly limited. Meanwhile, the probe unit 10a is made of metal having high heat conductivity and having strength allowing the probe unit 10a to endure sticking into a fine point of a plant such as stainless steel, aluminum, aluminum alloy, steel, iron, or titanium, for example. As a material for the first probe unit 10a, commercially-available metallic plates are usable such as steel plates used for beverage cans, etc., and aluminum plates, for example.

The position of the probe 12 relative to the heat transfer plate 11 is not particular limited. The probe 12 may be provided in an upright posture at the center of the heat transfer plate 11 or at an end of the heat transfer plate 11.

The heater 20 is a member having a function of generating heat. The heater 20 supplies heat to the first probe unit 10a. The heater 20 is provided at the heat transfer plate 11 in such a manner as to allow supply of heat to the heat transfer plate 11. The heater 20 may be provided to directly contact the heat transfer plate 11, or may be provided indirectly via another member therebetween.

The heater 20 preferably has a surface to form surface contact with the heat transfer plate 11. The heater 20 preferably has a shape and a size comparable to those of the heat transfer plate 11. In particular, the heater 20 preferably has an area same as or larger than that of the heat transfer plate 11. This increases an area of contact between the heater 20 and the heat transfer plate 11 to allow heat of the heater 20 to be supplied efficiently to the first probe unit 10a.

A micro ceramic heater is usable as the heater 20. The micro ceramic hater has a rectangular solid heat generation unit. The heat generation unit is formed by covering a heat generator with a ceramic material such as aluminum oxide. Various types of micro ceramic heaters including heat generation units of respective sizes are commercially available. Using a commercially-available micro ceramic heater as the heater 20 allows manufacture of the vascular sap flow speed sensor 1 at low cost.

A sheet having high heat conductivity may be interposed between the heat transfer plate 11 and the heater 20. This allows heat generated by the heater 20 to be transferred more efficiently to the heat transfer plate 11. This sheet may be a resin sheet containing a high heat conductive filler such as boron nitride or a super graphite sheet, for example.

The first temperature sensor 30a is a member having a function of measuring a temperature. The first temperature sensor 30a measures a temperature at the first probe unit 10a. The first temperature sensor 30a is provided at the heat transfer plate 11 in such a manner as to allow measurement of a temperature at the heat transfer plate 11. The first temperature sensor 30a may be provided to directly contact the heat transfer plate 11, or may be provided indirectly via another member therebetween.

The first temperature sensor 30a may be a sheet-like material provided with a temperature detection element such as a film temperature sensor, for example. The temperature sensor of this type is configured by inserting a thermocouple in a sheet-like material made of polyimide, for example. The thermocouple may be made of various types of material combinations such as a combination of platinum and platinum-rhodium, a combination of chromel and alumel, etc. The thermocouple may be replaced with a resistance temperature detector made of platinum, nickel, or copper, for example, or with a thermistor. A thermocouple or a resistance element may be formed on a surface of the sheet-like material by thin film technology. Using a commercially-available film temperature sensor as the first temperature sensor 30a allows manufacture of the vascular sap flow speed sensor 1 at low cost.

The first housing 40a includes a body 41 and a lid 42. The heater sensor HS is assembled by housing the heater 20, the first temperature sensor 30a, and the first probe unit 10a into the body 41, and closing the lid 42. The lid 42 is provided with a hole 43. The probe 12 passes through the hole 43 to be exposed to the outside of the first housing 40a. Thus, with the heater sensor HS in an assembled state, the heat transfer plate 11, the heater 20, and the first temperature sensor 30a are housed in the first housing 40a, and only the probe 12 is exposed to the outside of the first housing 40a.

The first housing 40a has a function of heat-insulating the members housed in the first housing 40a from external environment, a water resistant function, and a moisture resistant function. The first housing 40a suppresses temperature change at the first probe unit 10a or removal of heat of the heater 20 to be caused by the influence of rain or wind, for example. In the event of rain, the first housing 40a suppresses entry of water into the interior of the housing 40a. In this way, the measuring accuracy of the vascular sap flow speed sensor 1 can be enhanced.

The first housing 40a is preferably made of a material such as resin having lower heat conductivity than a material forming the first probe unit 10a. Using a material having low heat conductivity for forming the first housing 40a can achieve high heat insulating properties. Using resin for forming the first housing 40a allows manufacture of the first housing 40a at low cost.

The positions of the heater 20 and the first temperature sensor 30a relative to the heat transfer plate 11 are not particularly limited. The heater 20, the first temperature sensor 30a, and the heat transfer plate 11 may be stacked in this order. The heater 20 and the first temperature sensor 30a may be arranged closer to the upper surface of the heat transfer plate 11 (closer to the probe 12).

One of the heater 20 and the first temperature sensor 30a may be arranged closer to the lower surface of the heat transfer plate 11, and the other may be arranged closer to the upper surface of the heat transfer plate 11. This increases both an area of contact between the heater 20 and the heat transfer plate 11 and an area of contact between the first temperature sensor 30a and the heat transfer plate 11. This facilitates both transfer of heat between the first probe unit 10a and the heater 20 and transfer of heat between the first probe unit 10a and the first temperature sensor 30a. In particular, in many cases, a flexible printed board as a constituting member of the film temperature sensor is made of polyimide having high heat insulating properties. Hence, placing the film temperature sensor between the heater 20 and the heat transfer plate 11 makes it difficult to transfer heat of the heater 20 to the first probe unit 10a. In response to such a case, arranging the first temperature sensor 30a closer to the upper surface of the heat transfer plate 11 facilitates transfer of heat of the heater 20 to the first probe unit 10a.

The reference sensor RS includes a second probe unit 10b, a second temperature sensor 30b, and a second housing 40b. The second probe unit 10b includes a heat transfer plate 11 and a probe 12 provided in an upright posture at the heat transfer plate 11.

The configuration of the second probe unit 10b for the reference sensor RS can be the same as that of the first probe unit 10a for the heater sensor HS. Members used as the first probe unit 10a for the heater sensor HS and as the second probe unit 10b for the reference sensor RS generally have the same shape and the same size. Tip portions of the respective probes 12, 12 of the first probe unit 10a and the second probe unit 10b are to be located in a xylem or a phloem of a plant, so that the probes 12, 12 are required to have the same length. Where the first probe unit 10a and the second probe unit 10b are not to be distinguished from each other, these probe units will simply be called a probe unit 10.

The second temperature sensor 30b is a member having a function of measuring a temperature. The second temperature sensor 30b measures a temperature at the second probe unit 10b. The second temperature sensor 30b is formed at the heat transfer plate 11 in such a manner as to allow measurement of a temperature at the heat transfer plate 11. The second temperature sensor 30b may be provided to directly contact the heat transfer plate 11, or may be provided indirectly via another member therebetween. The structure of the second temperature sensor 30b can be the same as that of the first temperature sensor 30a. For example, the second temperature sensor 30b may be a sheet-like material provided with a temperature detection element.

The second housing 40b includes a body 41 and a lid 42. The reference sensor RS is assembled by housing the second temperature sensor 30b and the second probe unit 10b into the body 41, and closing the lid 42. The lid 42 is provided with a hole 43. The probe 12 passes through the hole 43 to be exposed to the outside of the second housing 40b. Thus, with the reference sensor RS in an assembled state, the heat transfer plate 11 and the second temperature sensor 30b are housed in the second housing 40b, and only the probe 12 is exposed to the outside of the second housing 40b.

The second housing 40b has a function of heat-insulating the members housed in the second housing 40b from external environment, a water resistant function, and a moisture resistant function. The second housing 40b suppresses temperature change at the second probe unit 10b to be caused by the influence of rain or wind, for example. In the event of rain, the second housing 40b suppresses entry of water into the interior of the housing 40b. In this way, the measuring accuracy of the vascular sap flow speed sensor 1 can be enhanced.

The second housing 40b is preferably made of a material such as resin having lower heat conductivity than a material forming the second probe unit 10b. Using a material having low heat conductivity for forming the second housing 40b can achieve high heat insulating properties. Using resin for forming the second housing 40b allows manufacture of the second housing 40b at low cost.

The position of the second temperature sensor 30b relative to the heat transfer plate 11 is not particularly limited. The second temperature sensor 30b may be arranged closer to the lower surface of the heat transfer plate 11. Alternatively, the second temperature sensor 30b may be arranged closer to the upper surface of the heat transfer plate 11.

(Manufacturing Method)

A method of manufacturing the vascular sap flow speed sensor 1 will be described next.

Manufacture of the vascular sap flow speed sensor 1 is largely divided into the following steps: (I) a probe unit forming step; (II) a heater sensor assembling step; and (III) a reference sensor assembling step. These steps will be described sequentially below.

(I) Probe Unit Forming Step

The probe unit forming step is a step of forming a plurality of probe units 10 using a metallic material. As a result of this step, two probe units 10, namely, the first probe unit 10a for the heater sensor HS and the second probe unit 10b for the reference sensor RS are obtained.

The probe unit forming step may be performed by four types of methods, namely, (1) a method using laser machining; (2) a method using stamping; (3) a method using deep drawing; and (4) a method using a wire rod. Of these methods, (1), (2), and (3) correspond to methods of forming the heat transfer plate 11 and the probe 12 through machining on a single metallic plate. Each of these methods will be described below. The probe unit 10 can be formed in any of the methods (1) to (4), or by other methods.

(1) Method Using Laser Machining

First, as shown in FIG. 3A, a metallic plate 50 is cut by laser machining to form a heat transfer plate corresponding part 51 and a probe corresponding part 52 (plate processing step). More specifically, the rectangular metallic plate 50 is cut at two corners into rectangles (cut along alternate long and short dashed lines in FIG. 3A), and then the corners are removed (hatched parts in FIG. 3A are removed). The metallic plate 50 may be a plate made of stainless steel, aluminum, aluminum alloy, steel, iron, or titanium, for example. A laser machine is used for the laser machining.

Next, as shown in FIG. 3B, the metallic plate 50 is caught between a die 61 having a V-shaped recess and a punch 62 having a V-shaped tip portion, and a connection between the heat transfer plate corresponding part 51 and the probe corresponding part 52 is bent (bending step).

As a result, the probe unit 10 having a shape shown in FIG. 3C is formed. This probe unit 10 is formed from the single metallic plate 50 with the heat transfer plate corresponding part 51 and the probe corresponding part 52, and the connection between the heat transfer plate corresponding part 51 and the probe corresponding part 52 is bent. By the implementation of this method, the probe 12 is arranged at an end of the heat transfer plate 11. Further, the probe 12 is formed into a prism. The probe 12 has the same thickness as the metallic plate 50.

As the probe unit 10 is formed from the single metallic plate 50, the probe unit 10 can be manufactured at low cost. As the probe unit 10 is formed by the laser machining and the bending on the metallic plate 50, the probe unit 10 can be manufactured at low cost. As the heat transfer plate 11 and the probe 12 are formed integrally, the probe unit 10 is unlikely to be broken.

A position of cutting the metallic plate 50 is not limited to the position shown in FIG. 3A. As shown in FIG. 4A, the rectangular metallic plate 50 may be cut from one end to the center of an edge (cut along alternate long and short dashed lines in FIG. 4A). Then, the probe corresponding part 52 is raised to form the probe unit 10 having a shape shown in FIG. 4B.

Figure 5A:
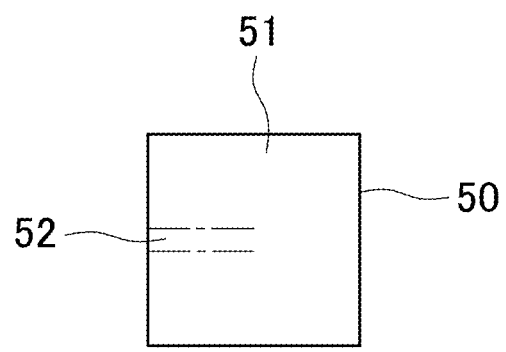
FIG. 5A is an explanatory view of laser machining.
Figure 5B:
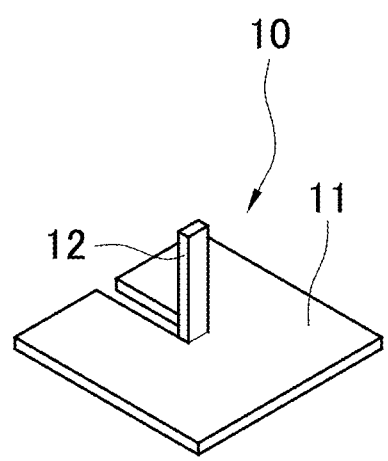
FIG. 5B is a perspective view of the probe unit.

As shown in FIG. 5A, the rectangular metallic plate 50 may be cut along two lines from the center of one side to the center of the metallic plate 50 (cut along alternate long and short dashed lines in FIG. 5A). Then, the probe corresponding part 52 is raised to form the probe unit 10 having a shape shown in FIG. 5B. In this case, the probe 12 is arranged at the center of the heat transfer plate 11.

(2) Method Using Stamping

First, as shown in FIG. 6A, a metallic plate 50 is stamped by pressing to form a heat transfer plate corresponding part 51 and a probe corresponding part 52 (plate processing step). More specifically, the metallic plate 50 is stamped into a shape with the probe corresponding part 52 connected to an end of the heat transfer plate corresponding part 51. A die allowing stamping into the foregoing shape is formed for the stamping.

Next, as shown in FIG. 6B, the metallic plate 50 is caught between a die 61 having a V-shaped recess and a punch 62 having a V-shaped tip portion, and a connection between the heat transfer plate corresponding part 51 and the probe corresponding part 52 is bent (bending step).

As a result, the probe unit 10 having a shape shown in FIG. 6C is formed. This probe unit 10 is formed from the single metallic plate 50 with the heat transfer plate corresponding part 51 and the probe corresponding part 52, and the connection between the heat transfer plate corresponding part 51 and the probe corresponding part 52 is bent. By the implementation of this method, the probe 12 is arranged at an end of the heat transfer plate 11. Further, the probe 12 is formed into a prism.

As the probe unit 10 is formed by stamping and bending on the metallic plate 50, this method is suitable for mass production and allows manufacture of the probe unit 10 at low cost. Further, as the heat transfer plate 11 and the probe 12 are formed integrally, the probe unit 10 is unlikely to be broken.

(3) Method Using Deep Drawing

Figure 7A:
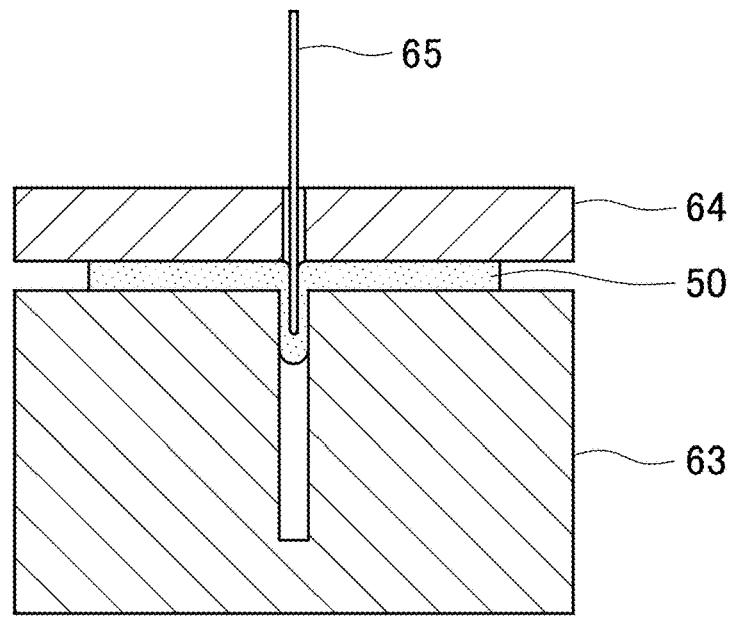
FIG. 7A is an explanatory view of deep drawing.
Figure 7B:
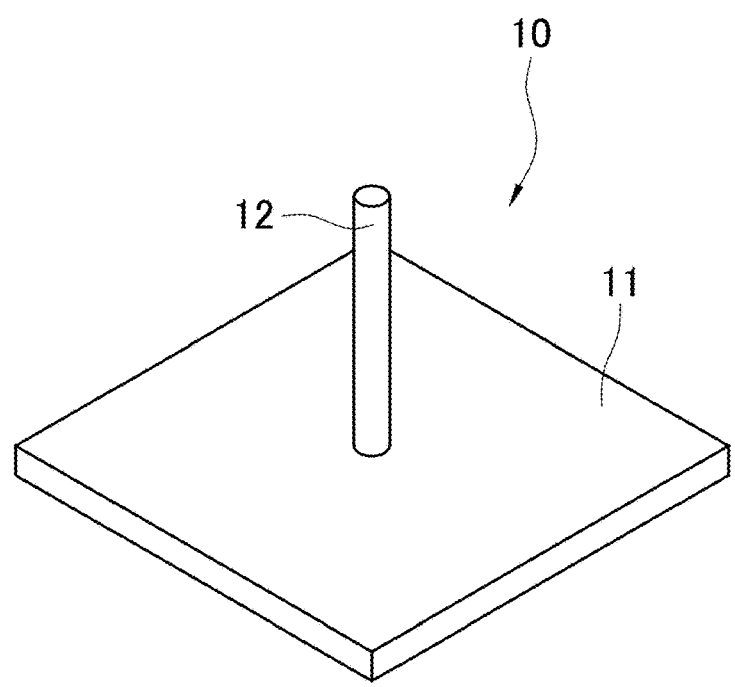
FIG. 7B is a perspective view of the probe unit.

As shown in FIG. 7A, a metallic plate 50 is caught between a die 63 and an anti-crease plate 64, and deep drawing is performed using a needle-like punch 65, thereby providing a projection as the probe 12. As a result, the probe unit 10 having a shape shown in FIG. 7B is formed. This probe unit 10 includes the heat transfer plate 11 and the probe 12 formed by providing the projection at a part of the single metallic plate 50. This method allows the probe 12 to be arranged at the center of the heat transfer plate 11. As the probe unit 10 is formed by providing the projection at a part of the metallic plate 50 by the deep drawing, the probe unit 10 can be manufactured at low cost. Further, as the heat transfer plate 11 and the probe 12 are formed integrally, the probe unit 10 is unlikely to be broken.

(4) Method Using Wire Rod

First, as shown in FIG. 8A, a metallic plate is cut to form a heat transfer plate corresponding part 51. Further, a metallic wire rod is cut into a predetermined length to form a probe corresponding part 52. Next, the probe corresponding part 52 in an upright posture is joined to the heat transfer plate corresponding part 51. Preferably, a hole 51*h* is formed at the heat transfer plate corresponding part 51 and an end portion of the probe corresponding part 52 is inserted into the hole 51*h*. A wire rod used as the metallic wire rod is not particularly limited but may be a commonly-used wire rod such as a stainless steel wire, an aluminum wire, an iron wire, a copper wire, a brass wire, a titanium wire, or a tungsten wire, for example. A method of joining the heat transfer plate corresponding part 51 and the probe corresponding part 52 is not particularly limited but it may be a method using welding, brazing and soldering, fitting, or a method using an adhesive, for example.

As a result, the probe unit 10 having a shape shown in FIG. 8B is formed. This probe unit 10 includes the heat transfer plate corresponding part 51 made of the metallic plate and the probe corresponding part 52 made of the metallic wire rod joined to each other. This method allows the probe 12 to be arranged at the center of the heat transfer plate 11. Further, the probe 12 can be formed into a circular columnar shape. As the probe unit 10 is formed using the metallic plate and the metallic wire rod, the probe unit can be manufactured at low cost. Further, the length of the probe 12 can be set freely only by changing a position of cutting the metallic wire rod.

(II) Heater Sensor Assembling Step

The heater sensor assembling step is a step of assembling various types of constituting members into the heater sensor HS. As shown in FIG. 2, the heater sensor HS is assembled by housing the heater 20, the first temperature sensor 30*a*, and the first probe unit 10*a* into the body 41 of the first housing 40*a*, and then closing the lid 42. The probe 12 passes through the hole 43 of the lid 42 to be exposed to the outside of the first housing 40*a*. The heat transfer plate 11, the heater 20, and the first temperature sensor 30*a* are housed in the first housing 40*a* to provide the heater 20 and the first temperature sensor 30*a* at the heat transfer plate 11.

(III) Reference Sensor Assembling Step

The reference sensor assembling step is a step of assembling various types of constituting members into the reference sensor RS. The reference sensor RS is assembled by housing the second temperature sensor 30*b* and the second probe unit 10*b* into the body 41 of the second housing 40*b*, and then closing the lid 42. The probe 12 passes through the hole 43 of the lid 42 to be exposed to the outside of the second housing 40*b*. The heat transfer plate 11 and the second temperature sensor 30*b* are housed in the second housing 40*b* to provide the second temperature sensor 30*b* at the heat transfer plate 11.

As described above, the vascular sap flow speed sensor 1 is configured using the simple constituting members and is manufactured by the simple steps. Thus, the vascular sap flow speed sensor 1 can be manufactured at low cost. Further, in the vascular sap flow speed sensor 1, the length of the probe 12 can be set freely in response to a stem diameter of a plant. This allows measurement of the flow speeds of vascular sap flows in plants of a variety of stem diameters.

(Method of Use)

Figure 9:
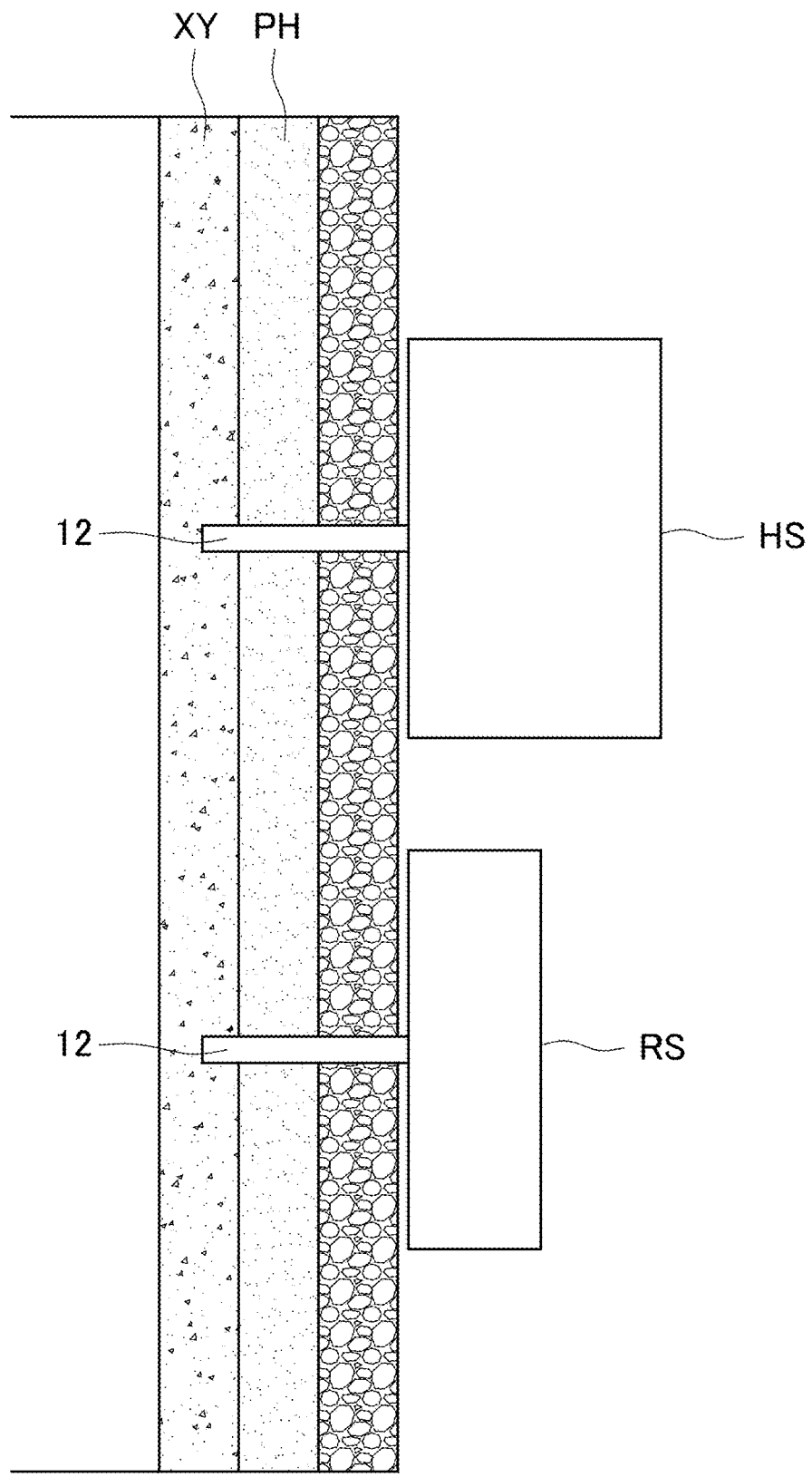
FIG. 9 is an explanatory view of the vascular sap flow speed sensor attached to a plant.

A method of using the vascular sap flow speed sensor 1 will be described next. First, the vascular sap flow speed sensor 1 is attached to a fine point of a plant as a measurement target. More specifically, as shown in FIG. 9, the respective probes 12 of the heater sensor HS and the reference sensor RS are stuck into the fine point of the plant. At this time, the probes 12, 12 are arranged along a vascular sap flow. The reference sensor RS is arranged on an upstream side of the vascular sap flow. The heater sensor HS is arranged on a downstream side of the vascular sap flow.

For measurement of the flow rate of xylem sap, a tip portion of each probe 12 is located in a xylem XY. The xylem sap generally flows in a direction from a root toward a distal end of a plant, so that the reference sensor RS is arranged closer to the root and the heater sensor HS is arranged closer to the distal end.

Next, the heater 20 provided at the heater sensor HS is actuated. By starting the heater 20, heat energy from the heater 20 is supplied to the probe 12 of the heater sensor HS. The heat energy supplied to the probe 12 of the heater sensor HS is emitted from a surface of the probe 12 to xylem sap flowing in the xylem XY.

Next, on the basis of temperatures measured by the heater sensor HS and the reference sensor RS, the flow rate (flow speed) of the xylem sap is measured according to the aforementioned Granier method. If the flow rate of the xylem sap is high (if the flow speed thereof is high), for example, xylem sap in the vicinity of the probe 12 of the heater sensor HS is always replaced by new xylem sap. Thus, if constant heat energy is supplied to the probe 12, the temperature of the probe 12 is reduced. By contrast, if the flow rate of the xylem sap is low (if the flow speed thereof is low), xylem sap stays in the vicinity of the probe 12 of the heater sensor HS. Thus, if constant heat energy is supplied to the probe 12, the temperature of the probe 12 is increased.

In this way, the flow speed and the flow rate of the xylem sap can be calculated on the basis of the temperature difference $\Delta T$ between temperatures measured by the heater sensor HS and the reference sensor RS. Locating the tip portions of the respective probes 12 of the heater sensor HS and the reference sensor RS in a phloem PH makes it possible to determine the flow speed and the flow rate of phloem sap.

The vascular sap flow speed sensor 1 of the first embodiment is also usable for measuring the flow speed of vascular sap using the heat pulse method.

The vascular sap flow speed sensor 1 includes the heater 20 and each of the temperature sensors 30a and 30b provided at the heat transfer plate 11 supporting the probe 12. This configuration facilitates transfer of heat between the probe 12 and the heater 20 and between the probe 12 and each of the temperature sensors 30a and 30b, compared to a conventional configuration in which a heater and a temperature sensor are directly provided at a probe. This can achieve size reduction of the probe 12 to allow measurement of the flow speed of vascular sap in a fine point of a plant.

Further, as the probe 12 can be reduced in size, even installing the probe 12 on a plant by sticking the probe 12 into the plant can still alleviate stress on the plant. In other words, reduction can be achieved in a change between before installation and after installation of the probe 12 with regard to the dynamics of vascular sap in the place of installation in the plant. This makes it possible to measure the dynamics of the vascular sap flowing in the place of the installation immediately after the probe 12 is stuck into the plant.

Further, as the probe 12 can be reduced in size, even when the vascular sap flow speed sensor 1 is installed on a plant, damage (injury) to the plant can still be alleviated. Thus, the vascular sap flow speed sensor 1 can be installed for a long period of time. As a result, the dynamics of vascular sap in the plant can be monitored for a long period of time, so that the plant can be supplied with water or replenished with nutrients (fertilized) appropriately in a manner that conforms to the growing condition of the plant.

By measuring the dynamics of vascular sap in a plant using the vascular sap flow speed sensor 1, the plant can be supplied with water or replenished with nutrients at the most appropriate times in accordance with the growing condition of the plant. This can contribute to increase in harvest of crops or fruit, and the like. Further, a water quantity in a new branch distal end or a pedicel of the plant can be measured, so that water supply can be controlled properly (water resources can be used effectively). This can achieve high-value added cultivation of fruit in terms of a high quality (high sugar content in a fruit) or stable production (equal quality), for example.

The probe unit 10 of the vascular sap flow speed sensor 1 of the first embodiment is formed by machining, so that the probe 12 can be formed into a relatively great length (for example, from 1 to 5 mm). This allows measurement of the flow speed of vascular sap in a plant in which a cortex is at a long distance from the xylem XY.

Second Embodiment

A vascular sap flow speed sensor 2 according to a second embodiment will be described next.

Figure 10:
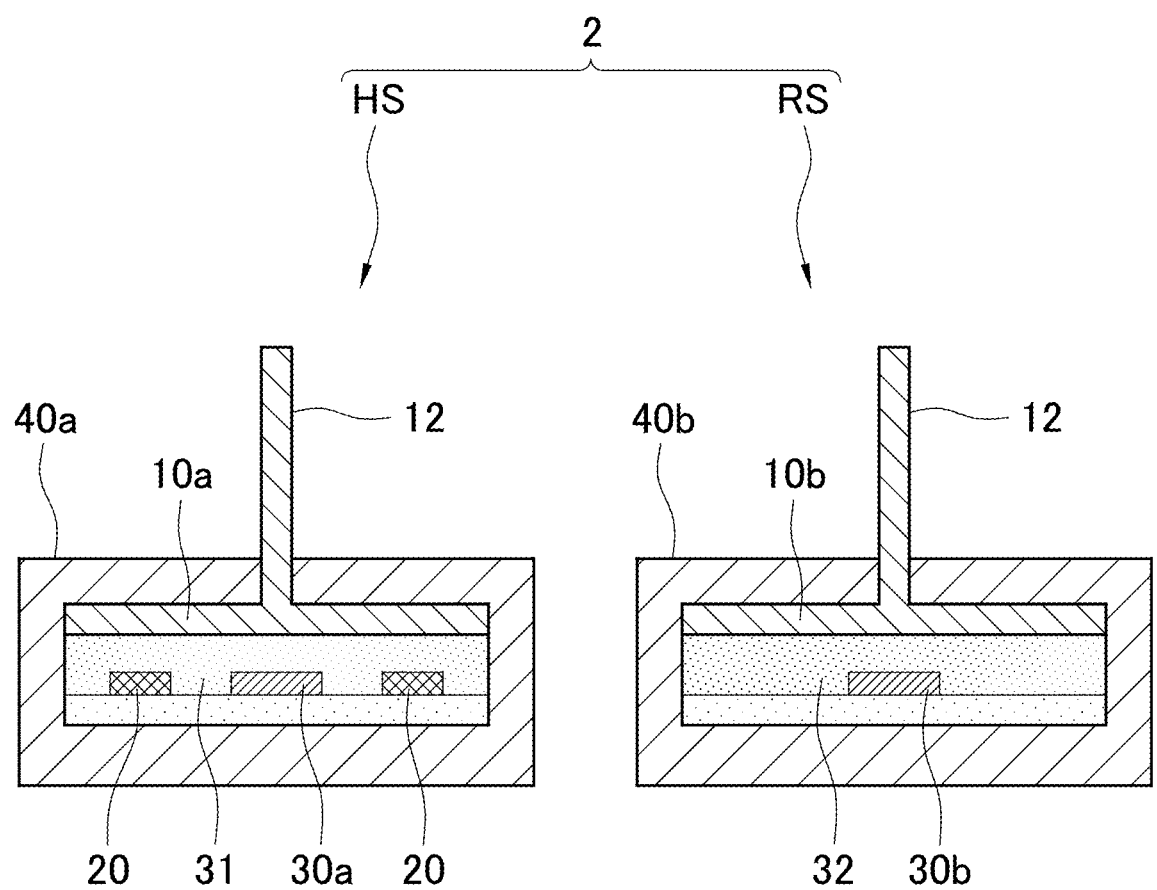
FIG. 10 is a longitudinal sectional view of a vascular sap flow speed sensor according to a second embodiment of this invention.

As shown in FIG. 10, the vascular sap flow speed sensor 2 includes the heater sensor HS and the reference sensor RS.

The heater sensor HS includes the first probe unit 10a, a heater and temperature sensor unit 31, and the first housing 40a. The heater and temperature sensor unit 31 is configured by forming the heater 20 and the first temperature sensor 30a on a semiconductor substrate. The heater and temperature sensor unit 31 preferably has an area same as or larger than that of the heat transfer plate 11.

A pn junction diode formed on the semiconductor substrate is usable as the heater 20. The pn junction diode can be formed by providing a diffusion hole (p type) at the semiconductor substrate and then forming n diffusion (n type). The heater 20 can be formed by providing a thin film of platinum (Pt), nichrome (NiCr), or an indium tin oxide material (ITO) on the semiconductor substrate by deposition or sputtering, for example, and forming the thin film into a predetermined shape. A pn junction diode formed on the semiconductor substrate is usable as the first temperature sensor 30a. A metallic film to become a thermocouple or a resistance temperature detector may be formed on the semiconductor substrate by thin film technology.

The reference sensor RS includes the second probe unit 10b, a temperature sensor unit 32, and the second housing 40b. The temperature sensor unit 32 is configured by forming the second temperature sensor 30b on a semiconductor substrate. The temperature sensor unit 32 preferably has an area same as or larger than that of the heat transfer plate 11. A pn junction diode formed on the semiconductor substrate is usable as the second temperature sensor 30b. A metallic film to become a thermocouple or a resistance temperature detector may be formed on the semiconductor substrate by thin film technology.

Forming the heater 20 and each of the temperature sensors 30a and 30b on the semiconductor substrate allows size reduction of each of the heater sensor HS and the reference sensor RS. Further, achieving mass production of the heater and temperature sensor units 31 and the temperature sensor units 32 allows manufacturing cost reduction.

Third Embodiment

A vascular sap flow speed sensor 3 according to a third embodiment will be described next.

Figure 11:
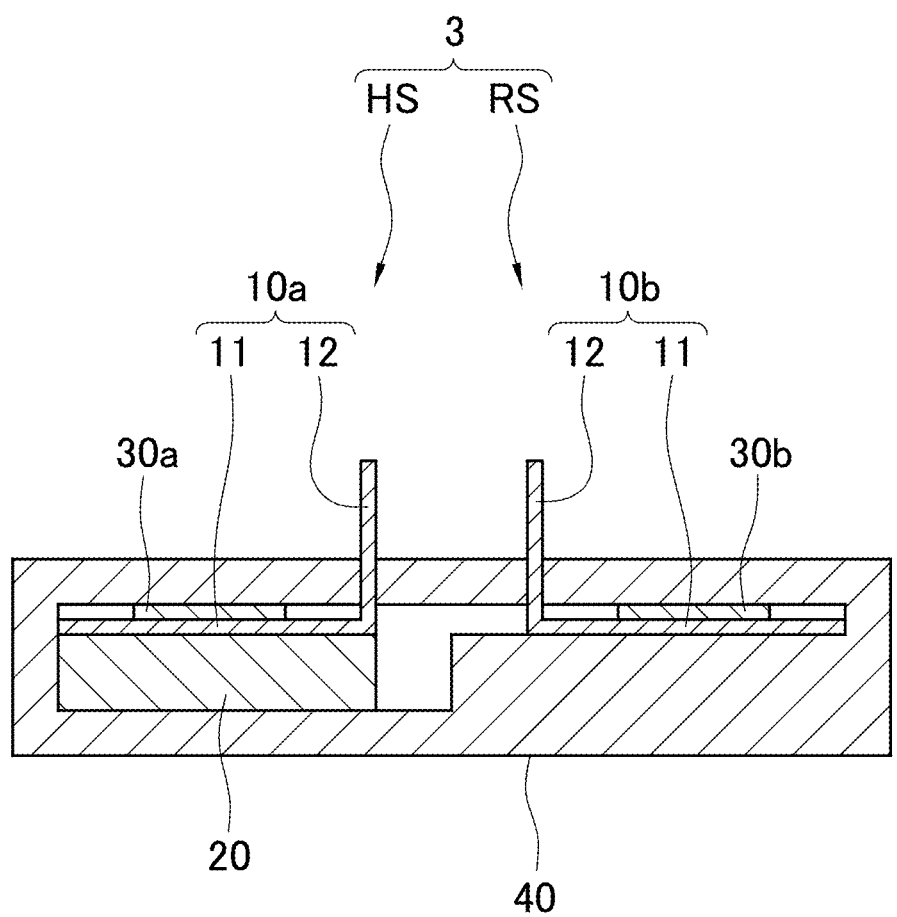
FIG. 11 is a longitudinal sectional view of a vascular sap flow speed sensor according to a third embodiment of this invention.

As shown in FIG. 11, the heater sensor HS and the reference sensor RS of the vascular sap flow speed sensor 3 are integrated with each other. The vascular sap flow speed sensor 3 includes a housing 40 with a first housing forming the heater sensor HS and a second housing forming the reference sensor RS, and the first housing and the second housing are integrated with each other. The probe 12 of the first probe unit 10a and the probe 12 of the second probe unit 10b are aligned along one surface of the housing 40.

As the two probes 12, 12 are arranged at one housing 40, the heater sensor HS and the reference sensor RS are provided as an integrated member. This allows the vascular sap flow speed sensor 3 to be attached easily to a plant.

If the probe unit 10 used herein is a probe unit in which the probe 12 is provided in an upright posture at an end of the heat transfer plate 11, the two probes 12 can be arranged in proximity to each other.

Fourth Embodiment

A vascular sap flow speed sensor 4 according to a fourth embodiment will be described next.

Figure 12:
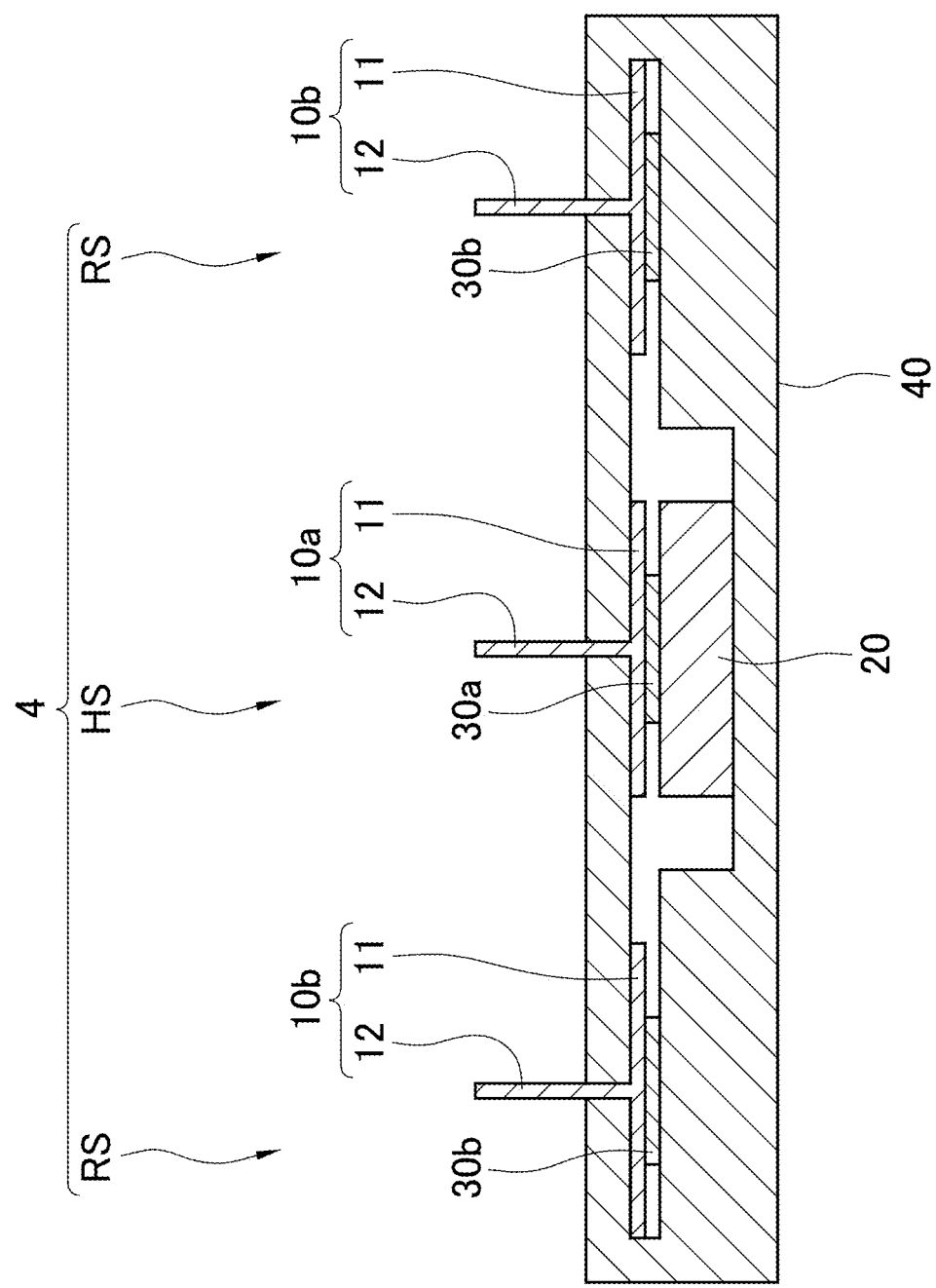
FIG. 12 is a longitudinal sectional view of a vascular sap flow speed sensor according to a fourth embodiment of this invention.

As shown in FIG. 12, the vascular sap flow speed sensor 4 includes one heater sensor HS and two reference sensors RS. Namely, the vascular sap flow speed sensor 4 includes three probe units 10. One of the probe units 10 is used as the heater sensor HS, and the two of the probe units 10 are used as the reference sensors RS.

The vascular sap flow speed sensor 4 includes a housing 40 with a first housing forming the heater sensor HS and two second housings forming the two reference sensors RS, and the first housing and the second housings are integrated with each other. The probe 12 of the first probe unit 10a and the probes 12, 12 of the two second probe units 10b, 10b are aligned along one surface of the housing 40. The probes 12, 12 of the two second probe units 10b, 10b are arranged at positions between which the probe 12 of the first probe unit 10a is located.

The vascular sap flow speed sensor 4 allows measurement not only of the flow rate of vascular sap but also of a direction in which the vascular sap flows. Further, the integrated configuration of the heater sensor HS and the reference sensors RS facilitates attachment of the vascular sap flow speed sensor 4 to a plant.

The vascular sap flow speed sensor 4 is attached to a plant in such a manner that the three probes 12 are located along a flow of vascular sap. After the heater 20 provided at the heater sensor HS is actuated, the heater sensor HS and the two reference sensors RS measure temperatures. A direction of the vascular sap can be specified by comparing the temperatures measured by the two reference sensors RS.

The two reference sensors RS are provided at positions between which the heater sensor HS is located. Thus, the probe 12 of the reference sensor RS located on a downstream side of a vascular sap flow is warmed by the vascular sap increased in temperature by the heater sensor HS. As a result, the probe 12 of the reference sensor RS on the downstream side of the vascular sap flow is placed at a higher temperature than the probe 12 of the reference sensor RS on an upstream side.

By using this phenomenon, a direction in which the vascular sap flows is specified by comparing the temperatures measured by the two reference sensors RS. A direction in which the vascular sap flows corresponds to a direction in which the vascular sap travels from the reference sensor RS at a lower temperature toward the reference sensor RS at a higher temperature.

EXAMPLES

A pseudo-plant experiment and a real plant experiment were conducted using the vascular sap flow speed sensor 1 shown in FIG. 1.

(Pseudo-Plant Experiment)

Figure 13:
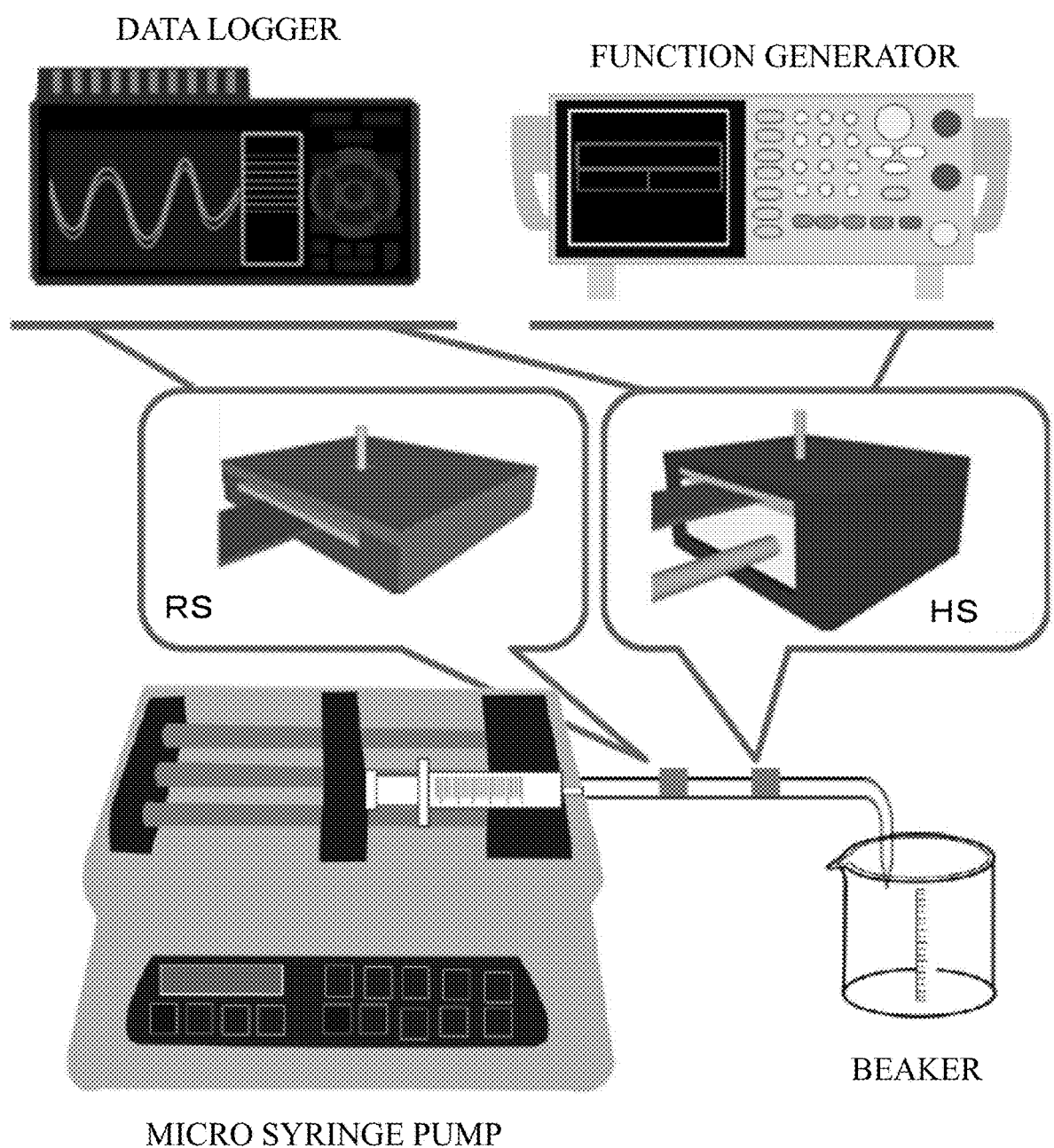
FIG. 13 is an explanatory view of a pseudo-plant experimental system.

The experiment was conducted using a pseudo-plant experimental system shown in FIG. 13. A pseudo vascular bundle was formed by flowing water into a silicone tube (an inner diameter of 2 mm and an outer diameter of 3 mm) with a micro syringe pump. The respective probes 12 of the heater sensor HS and the reference sensor RS were stuck into this pseudo vascular bundle. A flow rate in the silicone tube can be controlled precisely using the micro syringe pump. A function generator was used as a power supply for the heater 20 of the heater sensor HS. A data logger was used for acquiring data from the temperature sensors 30a and 30b of the heater sensor HS and the reference sensor RS respectively.

Figure 14:
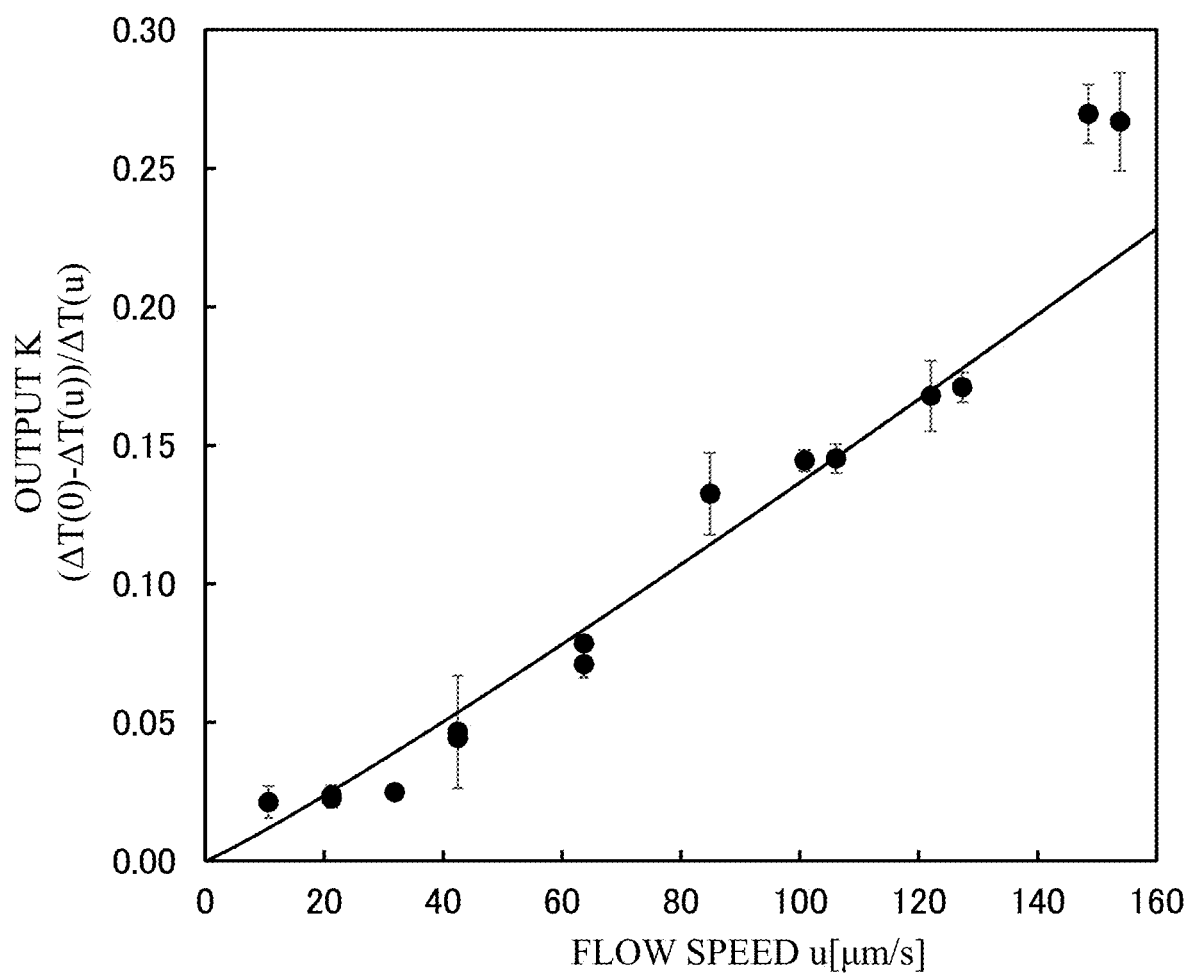
FIG. 14 is a graph showing a relationship between a flow speed u in a silicone tube and a K value obtained by a pseudo-plant experiment.

FIG. 14 is a graph showing a relationship between a flow speed u in the silicone tube and a K value. The flow speed u in the silicone tube can be determined from a flow rate in the micro syringe pump. The K value is determined from a temperature difference between the first temperature sensor 30a and the second temperature sensor 30b (see the formula (1)). Measured values were subjected to fitting using the formula (1) to determine coefficients. As a result, the following values were obtained. In this way, using the vascular sap flow speed sensor 1 was confirmed to be usable for measuring the flow rate of vascular sap.

$$1/\alpha = 6.20 \times 10^{-4}$$

$$1/\beta = 0.92$$

(Real Plant Experiment)

Eupatorium was used as a plant of a measurement target. The respective probes 12 of the heater sensor HS and the reference sensor RS were stuck into a stem of eupatorium. The probes 12 were stuck in such a manner as to locate respective tip portions of the probes 12 in a xylem. A function generator was used as a power supply for the heater 20 of the heater sensor HS. A data logger was used for acquiring data from the temperature sensors 30a and 30b of the heater sensor HS and the reference sensor RS respectively.

While the flow speed of xylem sap was measured using the vascular sap flow speed sensor 1, night-time and daytime were reproduced. Night-time was reproduced by covering the periphery of eupatorium with a cardboard for light shield. Daytime was reproduced by removing the cardboard and irradiating eupatorium with light from a fluorescent lamp. First, night-time was reproduced for one hour, then daytime was reproduced for one hour, and then night-time was reproduced for 15 minutes.

Figure 15:
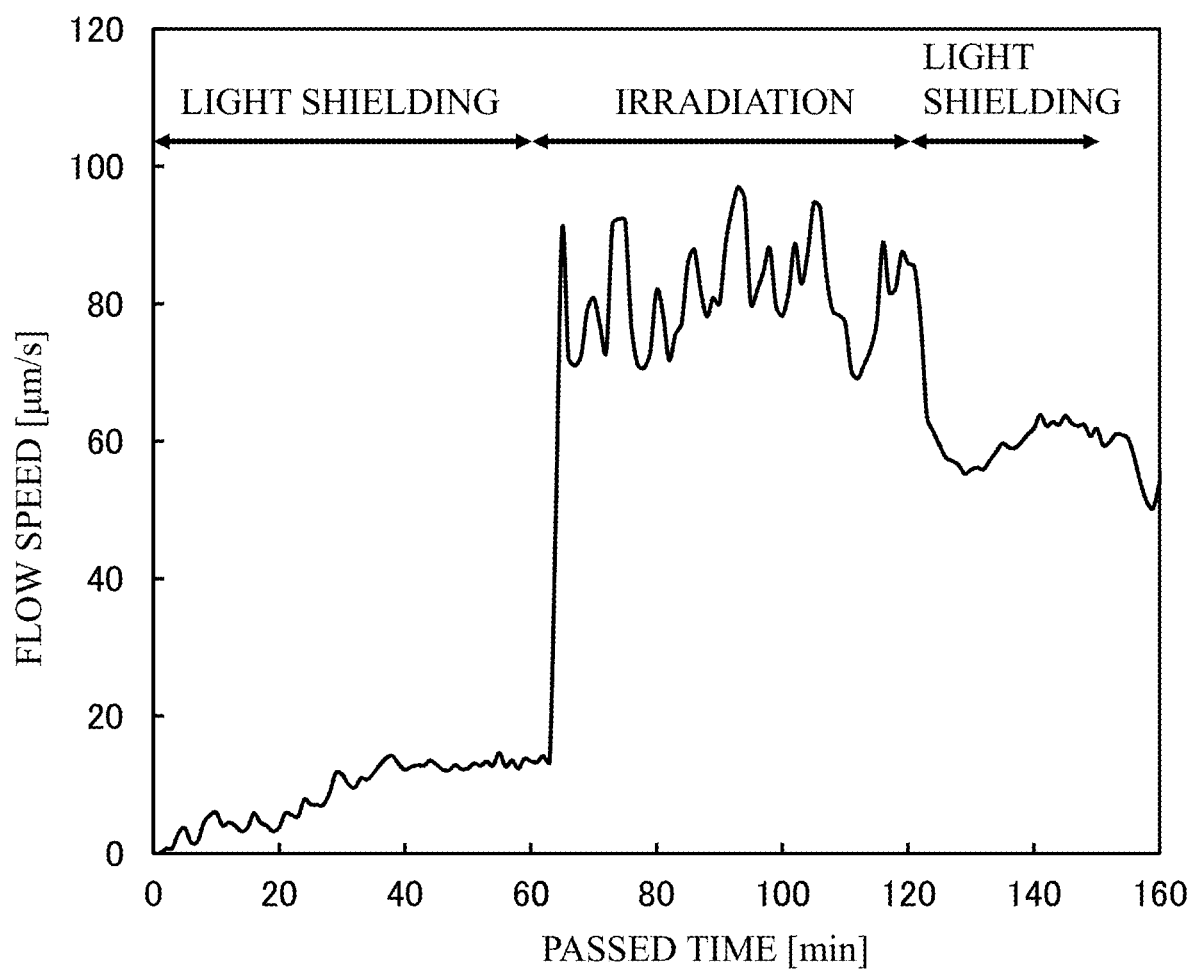
FIG. 15 is a graph showing a relationship between passed time and the flow speed of xylem sap obtained by a real plant experiment.

FIG. 15 is a graph showing a relationship between passed time and the flow speed of the xylem sap. As understood from FIG. 15, the flow speed of the xylem sap is reduced during the light shielding, whereas the flow speed of the xylem sap is increased during the irradiation with light from the fluorescent lamp. Generally, irradiating a plant with light causes photosynthesis and causes the plant to suck up water, thereby increasing the flow speed of xylem sap. This experiment was confirmed to be usable for reproducing such characteristics of plants. Further, the vascular sap flow speed sensor 1 was confirmed to be usable for measuring the flow speed of xylem sap in real time.

REFERENCE SIGNS LIST 1, 2, 3, 4 Vascular sap flow speed sensor
HS Heater sensor
10a First probe unit
11 Heat transfer plate
12 Probe
20 Heater
30a First temperature sensor
40a First housing
RS Reference sensor
10b Second probe unit
30b Second temperature sensor
40b Second housing

The invention claimed is:

1. A vascular sap flow speed sensor, comprising:
a heater sensor; and
two reference sensors, wherein
the heater sensor comprises:
a first probe unit including a heat transfer plate and a probe provided in an upright posture at the heat transfer plate;
a heater that supplies heat to the heat transfer plate of the first probe unit;
a first temperature sensor that measures a temperature at the heat transfer plate of the first probe unit; and
a first housing in which the heat transfer plate of the first probe unit, the heater, and the first temperature sensor are housed and from which the probe of the first probe unit is exposed to the outside,
each of the two reference sensors comprises:
a second probe unit including a heat transfer plate and a probe provided in an upright posture at the heat transfer plate;
a second temperature sensor that measures a temperature at the heat transfer plate of the second probe unit; and
a second housing in which the heat transfer plate of the second probe unit and the second temperature sensor are housed and from which the probe of the second probe unit is exposed to the outside,
the probe of the first probe unit and the probe of the second probe unit have the same length,
each of the first probe unit and the second probe unit is made of a metallic material, and
the two reference sensors are arranged at positions between which the heater sensor is located during attachment to a plant.

2. The vascular sap flow speed sensor according to claim 1, wherein the length of each of the probe of the first probe unit and the probe of the second probe unit is from 1 to 5 mm.

3. The vascular sap flow speed sensor according to claim 1, comprising:
a housing with the first housing and the two second housings integrated with each other, wherein
the probe of the first probe unit and the probes of the two second probe units are aligned along one surface of the housing, and
the probes of the two second probe units are arranged at positions between which the probe of the first probe unit is located.

4. The vascular sap flow speed sensor according to claim 1, wherein each of the first probe unit and the second probe unit is formed by machining a single metallic plate into the heat transfer plate and the probe.

5. The vascular sap flow speed sensor according to claim 4, wherein each of the first probe unit and the second probe unit is made of the single metallic plate with a heat transfer plate corresponding part and a probe corresponding part, and a connection between the heat transfer plate corresponding part and the probe corresponding part is bent.

6. The vascular sap flow speed sensor according to claim 1, wherein the heater has an area same as or larger than that of the heat transfer plate of the first probe unit.

7. The vascular sap flow speed sensor according to claim 1, wherein each of the first temperature sensor and the second temperature sensor is a sheet-like material provided with a temperature detection element.

8. The vascular sap flow speed sensor according to claim 1, wherein the heater and the first temperature sensor are formed on a semiconductor substrate having an area same as or larger than that of the heat transfer plate of the first probe unit.

9. The vascular sap flow speed sensor according to claim 1, wherein the second temperature sensor is formed on a semiconductor substrate having an area same as or larger than that of the heat transfer plate of the second probe unit.

10. The vascular sap flow speed sensor according to claim 1, wherein each of the first housing and the second housing is made of a material having lower heat conductivity than a material forming each of the first probe unit and the second probe unit.

11. A vascular sap flow speed sensor comprising:
a heater sensor; and
a reference sensor,
wherein the heater sensor comprises:
a first probe unit including a heat transfer plate and a probe provided in an upright posture at the heat transfer plate;
a heater that supplies heat to the heat transfer plate of the first probe unit;
a first temperature sensor that measures a temperature at the heat transfer plate of the first probe unit; and
a first housing in which the heat transfer plate of the first probe unit, the heater, and the first temperature sensor are housed and from which the probe of the first probe unit is exposed to the outside,
the reference sensor comprises:
a second probe unit including a heat transfer plate and a probe provided in an upright posture at the heat transfer plate;
a second temperature sensor that measures a temperature at the heat transfer plate of the second probe unit; and a second housing in which the heat transfer plate of the second probe unit and the second temperature sensor are housed and from which the probe of the second probe unit is exposed to the outside, the probe of the first probe unit and the probe of the second probe unit have the same length, and each of the first probe unit and the second probe unit includes the heat transfer plate and the probe formed by providing a projection at a part of the single metallic plate by deep drawing.

12. A vascular sap flow speed sensor comprising:
a heater sensor; and
a reference sensor,
wherein the heater sensor comprises:
a first probe unit including a heat transfer plate and a probe provided in an upright posture at the heat transfer plate;
a heater that supplies heat to the heat transfer plate of the first probe unit;
a first temperature sensor that measures a temperature at the heat transfer plate of the first probe unit; and
a first housing in which the heat transfer plate of the first probe unit, the heater, and the first temperature sensor are housed and from which the probe of the first probe unit is exposed to the outside,
the reference sensor comprises:
a second probe unit including a heat transfer plate and a probe provided in an upright posture at the heat transfer plate;
a second temperature sensor that measures a temperature at the heat transfer plate of the second probe unit; and
a second housing in which the heat transfer plate of the second probe unit and the second temperature sensor are housed and from which the probe of the second probe unit is exposed to the outside,
the probe of the first probe unit and the probe of the second probe unit have the same length, and
each of the first probe unit and the second probe unit is formed by joining a probe corresponding part made of a metallic wire rod to a heat transfer plate corresponding part made of a metallic plate.

13. A method of manufacturing a vascular sap flow speed sensor, comprising:
a probe unit forming step of obtaining a first probe unit and a second probe unit by forming a plurality of probe units each including a heat transfer plate and a probe provided in an upright posture at the heat transfer plate using a metallic material;
a heater sensor assembling step of assembling a heater sensor by providing a heater and a first temperature sensor at the heat transfer plate of the first probe unit, and housing the heat transfer plate of the first probe unit, the heater, and the first temperature sensor into a first housing in such a manner as to expose the probe of the first probe unit to the outside from the first housing;
a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing; and
configuring the vascular sap flow speed sensor using the heater sensor, and the two reference sensors arranged at positions between which the heater sensor is located during attachment to a plant.

14. The method of manufacturing the vascular sap flow speed sensor according to claim 13, wherein the probe unit forming step comprises:
a plate processing step of processing a metallic plate to form a heat transfer plate corresponding part and a probe corresponding part; and
a bending step of bending a connection between the heat transfer plate corresponding part and the probe corresponding part.

15. The method of manufacturing the vascular sap flow speed sensor according to claim 14, wherein in the plate processing step, the metallic plate is cut by laser machining to form the heat transfer plate corresponding part and the probe corresponding part.

16. The method of manufacturing the vascular sap flow speed sensor according to claim 14, wherein in the plate processing step, the metallic plate is stamped by pressing to form the heat transfer plate corresponding part and the probe corresponding part.

17. A method of manufacturing a vascular sap flow speed sensor comprising:
a probe unit forming step of obtaining a first probe unit and a second probe unit by forming a plurality of probe units each including a heat transfer plate and a probe provided in an upright posture at the heat transfer plate using a metallic material;
a heater sensor assembling step of assembling a heater sensor by providing a heater and a first temperature sensor at the heat transfer plate of the first probe unit, and
housing the heat transfer plate of the first probe unit, the heater, and the first temperature sensor into a first housing in such a manner as to expose the probe of the first probe unit to the outside from the first housing; and
a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing
wherein the probe unit forming step comprises a step of providing a projection as the probe by performing deep drawing on a metallic plate.

18. A method of manufacturing a vascular sap flow speed sensor comprising:
a probe unit forming step of obtaining a first probe unit and a second probe unit by forming a plurality of probe units each including a heat transfer plate and a probe provided in an upright posture at the heat transfer plate using a metallic material;
a heater sensor assembling step of assembling a heater sensor by providing a heater and a first temperature sensor at the heat transfer plate of the first probe unit, and housing the heat transfer plate of the first probe unit, the heater, and the first temperature sensor into a first housing in such a manner as to expose the probe of the first probe unit to the outside from the first housing; and
a reference sensor assembling step of assembling a reference sensor by providing a second temperature sensor at the heat transfer plate of the second probe unit, and housing the heat transfer plate of the second probe unit and the second temperature sensor into a second housing in such a manner as to expose the probe of the second probe unit to the outside from the second housing wherein the probe unit forming step comprises:

a step of cutting a metallic plate to form a heat transfer plate corresponding part;

a step of cutting a metallic wire rod to form a probe corresponding part; and a step of joining the probe corresponding part to the heat transfer plate corresponding part.

* * * * *